United States Patent
Lee et al.

(10) Patent No.: US 10,086,325 B2
(45) Date of Patent: Oct. 2, 2018

(54) MEMBRANE SEPARATION DEVICE

(71) Applicant: LG CHEM, LTD., Seoul (KR)

(72) Inventors: Sang Beom Lee, Daejeon (KR); Moon Kyoon Chun, Daejeon (KR); Sung Ho Lee, Daejeon (KR); Jong Ku Lee, Daejeon (KR); Joon Ho Shin, Daejeon (KR)

(73) Assignee: LG Chem, Ltd., Seoul (KR)

(*) Notice: Subject to any disclaimer, the term of this patent is extended or adjusted under 35 U.S.C. 154(b) by 349 days.

(21) Appl. No.: 14/652,689

(22) PCT Filed: Feb. 19, 2014

(86) PCT No.: PCT/KR2014/001349
§ 371 (c)(1),
(2) Date: Jun. 16, 2015

(87) PCT Pub. No.: WO2014/129801
PCT Pub. Date: Aug. 28, 2014

(65) Prior Publication Data
US 2015/0321140 A1 Nov. 12, 2015

(30) Foreign Application Priority Data

Feb. 19, 2013 (KR) .................... 1 0-201 3-001 7624
Jun. 18, 2013 (KR) ........................ 10-2013-0069799
Jun. 18, 2013 (KR) ........................ 10-2013-0069800

(51) Int. Cl.
*B01D 53/22* (2006.01)
*C08J 9/14* (2006.01)
(Continued)

(52) U.S. Cl.
CPC ......... *B01D 53/225* (2013.01); *B01D 53/226* (2013.01); *B01D 53/228* (2013.01);
(Continued)

(58) Field of Classification Search
CPC ............. B01D 63/00; B01D 2311/263; B01D 2311/2646; B01D 2257/708;
(Continued)

(56) References Cited

U.S. PATENT DOCUMENTS 4,203,734 A * 5/1980 Winter .................. B01D 53/04
95/115
4,522,725 A * 6/1985 Koyama .............. B01D 61/145
210/639
(Continued)

FOREIGN PATENT DOCUMENTS

CN          1606492 A     4/2005
CN        101073742 A    11/2007
(Continued)

OTHER PUBLICATIONS

PERRY "Perrys-Chemical-Engineers-handbook" 7th Ed. 1997 McGraw-Hill, p. 22-64.*

*Primary Examiner* — Anthony Shumate
(74) *Attorney, Agent, or Firm* — Dentons US LLP

(57) ABSTRACT

The present application relates to a membrane separation device. According to the separation device of the present application, components to be separated using a separation membrane having a small area size can be separated with high selectivity and consequently processing efficiency and economical efficiency can be superbly improved; and according to a method for producing an expanded polystyrene which includes the membrane separation device, components to be separated using a separation membrane having a small area size, in particular, a volatile organic compound (VOC), can be separated with high selectivity and consequently processing efficiency and economical efficiency can be superbly improved, and also, by separating and recovering VOC, an effect in preventing environmental pollution caused by global warming is exhibited.

9 Claims, 8 Drawing Sheets

(51) Int. Cl.
  *B01J 19/24* (2006.01)
  *C07C 7/144* (2006.01)
  *C07C 7/00* (2006.01)
  *B01D 63/00* (2006.01)
  *C08F 6/12* (2006.01)

(52) U.S. Cl.
  CPC .............. *B01D 63/00* (2013.01); *B01J 19/24* (2013.01); *C07C 7/005* (2013.01); *C07C 7/144* (2013.01); *C08F 6/12* (2013.01); *C08J 9/141* (2013.01); *B01D 2053/221* (2013.01); *B01D 2257/708* (2013.01); *B01D 2311/25* (2013.01); *B01D 2311/263* (2013.01); *B01D 2311/2646* (2013.01); *B01D 2317/022* (2013.01); *B01D 2317/08* (2013.01); *B01D 2319/06* (2013.01); *B01J 2219/24* (2013.01); *C08J 2325/06* (2013.01)

(58) Field of Classification Search
  CPC .......... B01D 2311/25; B01D 2317/022; B01D 53/228; B01D 53/225; B01D 2053/221; B01D 53/226; B01D 2317/08; B01D 2319/06; C08F 6/12; C08J 2325/06; C08J 9/141; C07C 7/005; C07C 7/144; B01J 2219/24; B01J 19/24
  See application file for complete search history.

(56) References Cited

U.S. PATENT DOCUMENTS

| | | | | |
|---|---|---|---|---|
| 4,659,343 A | * | 4/1987 | Kelly | B01D 53/22 210/640 |
| 4,936,887 A | | 6/1990 | Waldo et al. | |
| 5,569,381 A | * | 10/1996 | Kuntz | B01D 21/0006 210/295 |
| 6,016,177 A | * | 1/2000 | Motomura | G02B 5/3033 349/175 |
| 6,565,626 B1 | * | 5/2003 | Baker | B01D 53/226 95/47 |
| 2002/0051264 A1 | * | 5/2002 | Shiozawa | G07D 7/0032 359/2 |
| 2002/0152889 A1 | | 10/2002 | Baker et al. | |
| 2002/0195250 A1 | * | 12/2002 | Underdown | B01D 53/22 166/357 |
| 2004/0099138 A1 | | 5/2004 | Karode et al. | |
| 2004/0099597 A1 | * | 5/2004 | Jitariouk | B01D 53/22 210/321.79 |
| 2005/0045029 A1 | * | 3/2005 | Coiling | B01D 53/225 95/46 |
| 2005/0068620 A1 | * | 3/2005 | Umeya | G03B 21/602 359/459 |
| 2007/0046595 A1 | * | 3/2007 | Gan | G02F 1/13476 345/87 |
| 2010/0212501 A1 | * | 8/2010 | Peters | B01D 53/22 96/8 |
| 2013/0098242 A1 | * | 4/2013 | Ungerank | B01D 53/226 95/51 |
| 2014/0374333 A1 | * | 12/2014 | Minoda | G01N 30/92 210/198.3 |
| 2015/0273388 A1 | * | 10/2015 | Fukuda | B01D 53/226 95/45 |

FOREIGN PATENT DOCUMENTS

| | | | |
|---|---|---|---|
| CN | 201337877 Y | 11/2008 | |
| EP | 0247585 A1 | 12/1987 | |
| KR | 100711237 B1 | 4/2007 | |
| WO | WO 2006044255 A2 * | 4/2006 | ......... B01D 19/0031 |

* cited by examiner

【Figure 1】
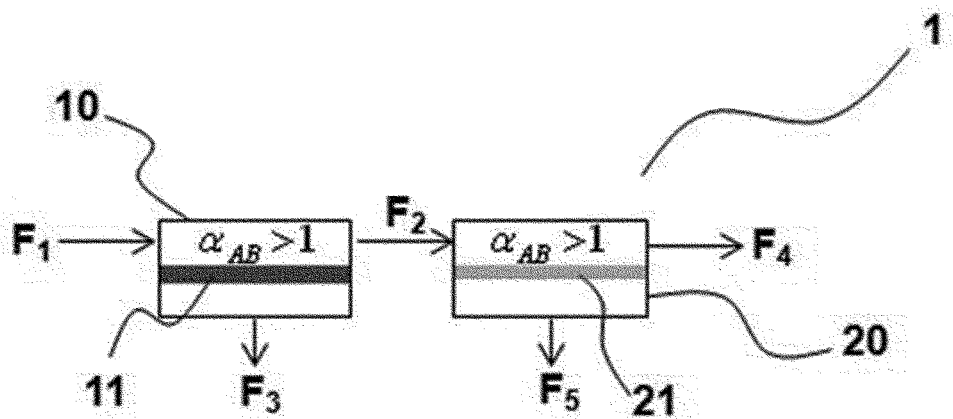
【Figure 2】
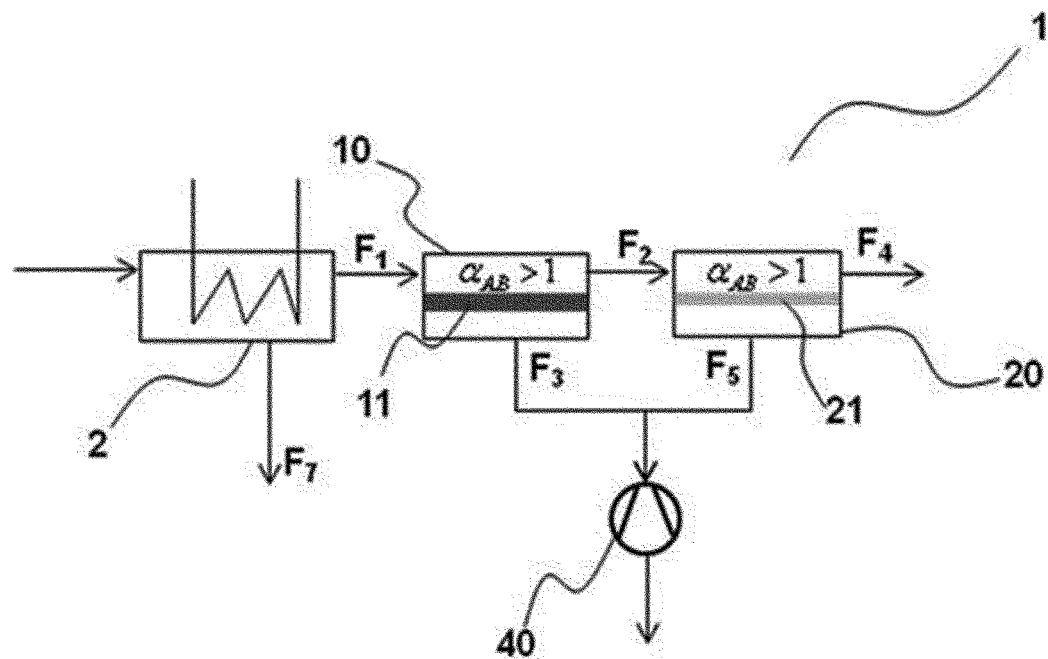

【Figure 3】
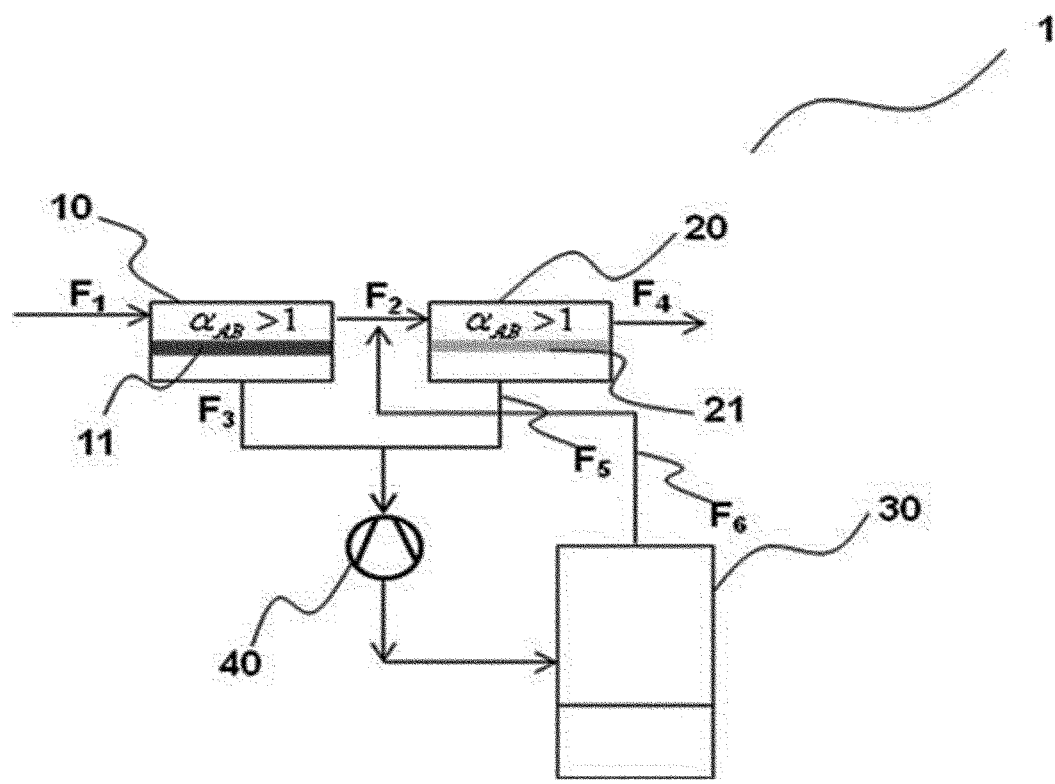

【Figure 4】
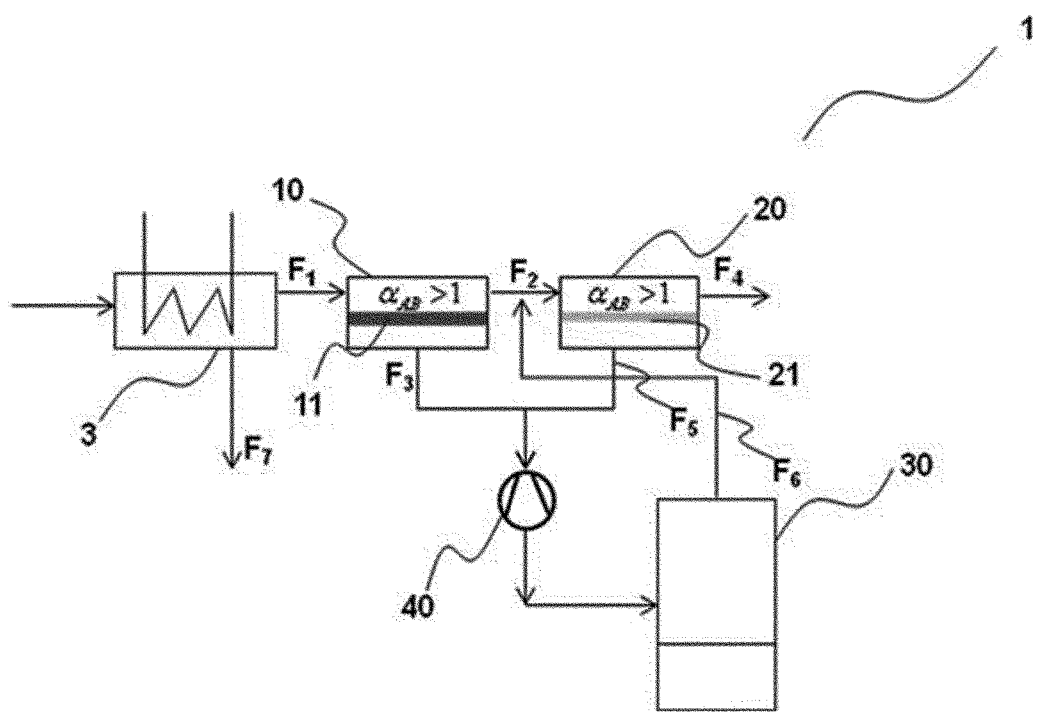

【Figure 5】
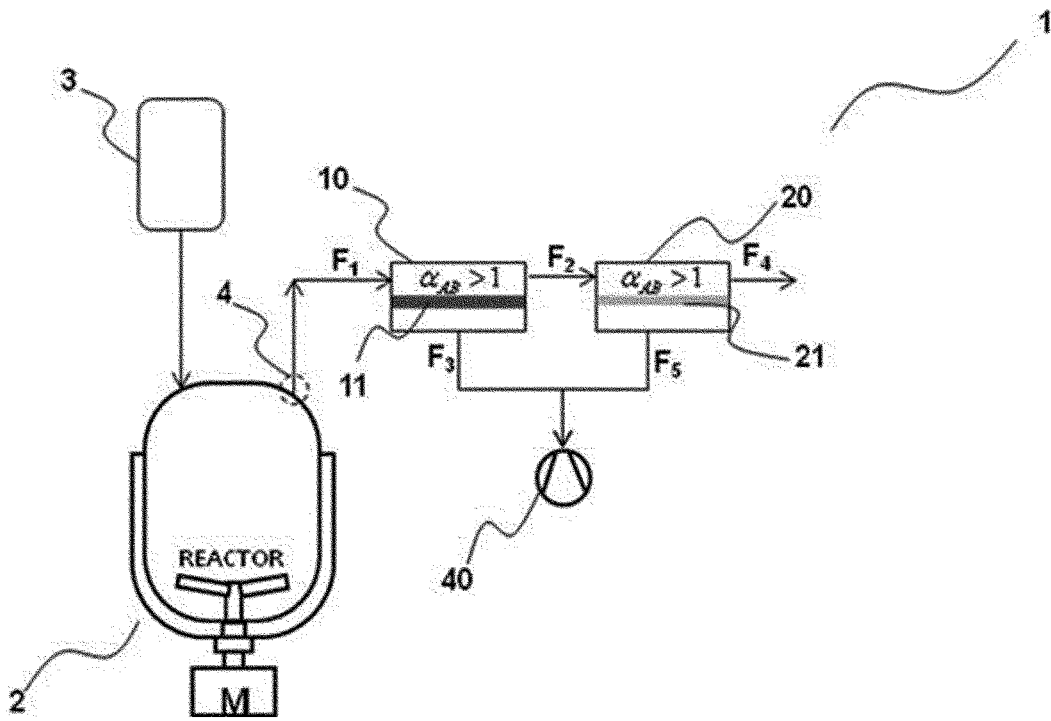
【Figure 6】
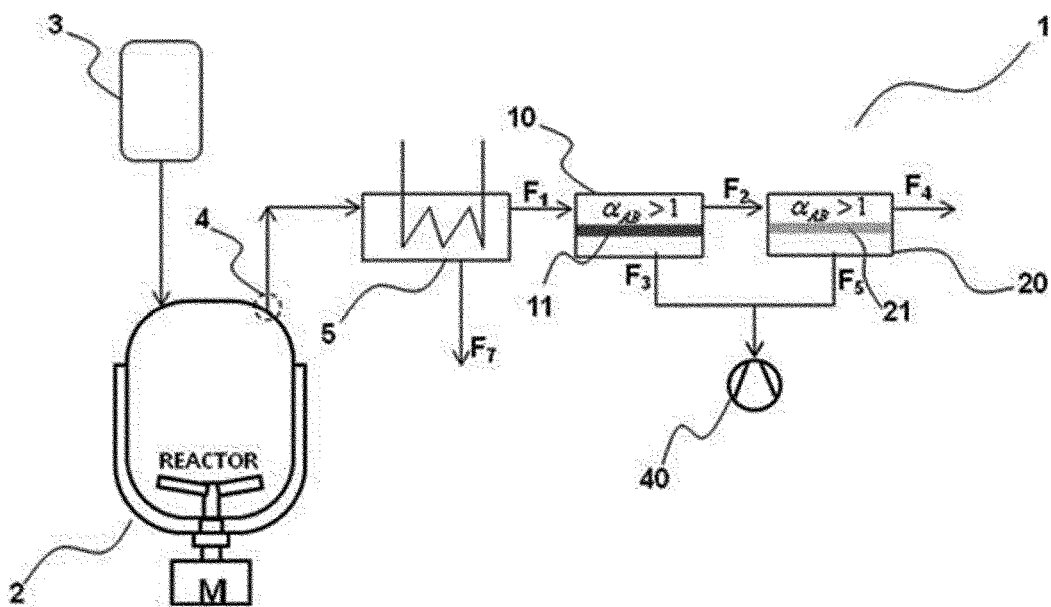

【Figure 7】
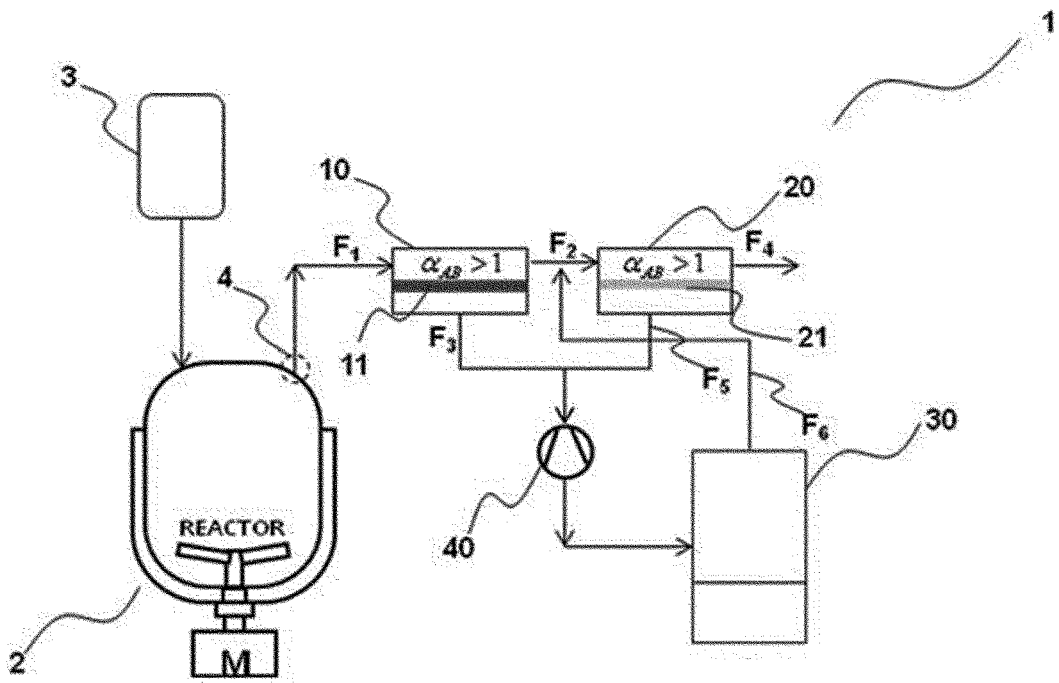
【Figure 8】
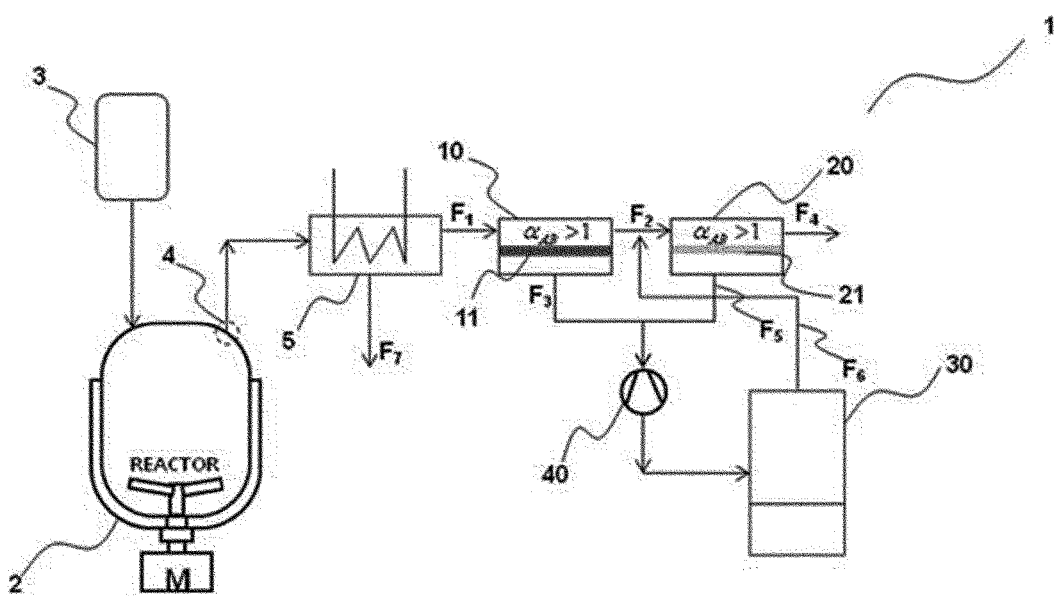

[Figure 9]
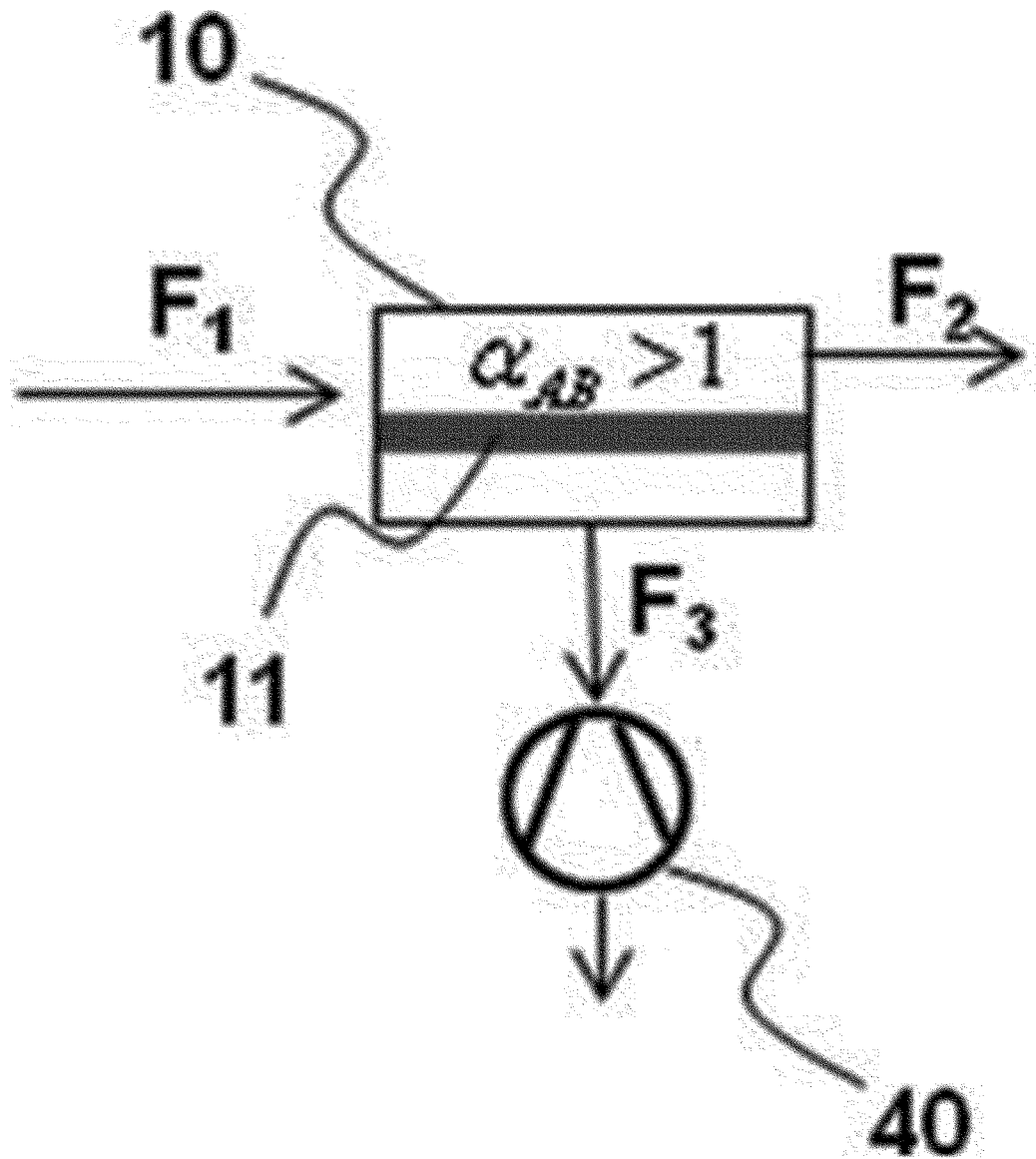

【Figure 10】
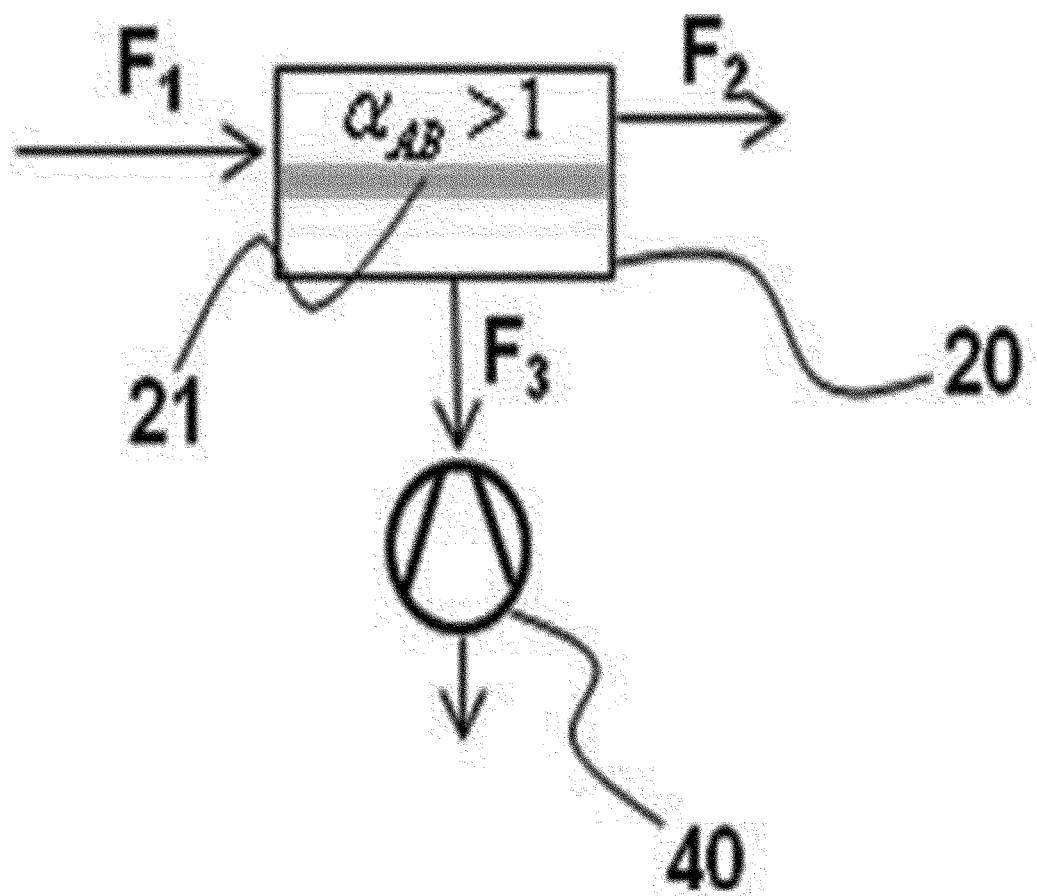

【Figure 11】
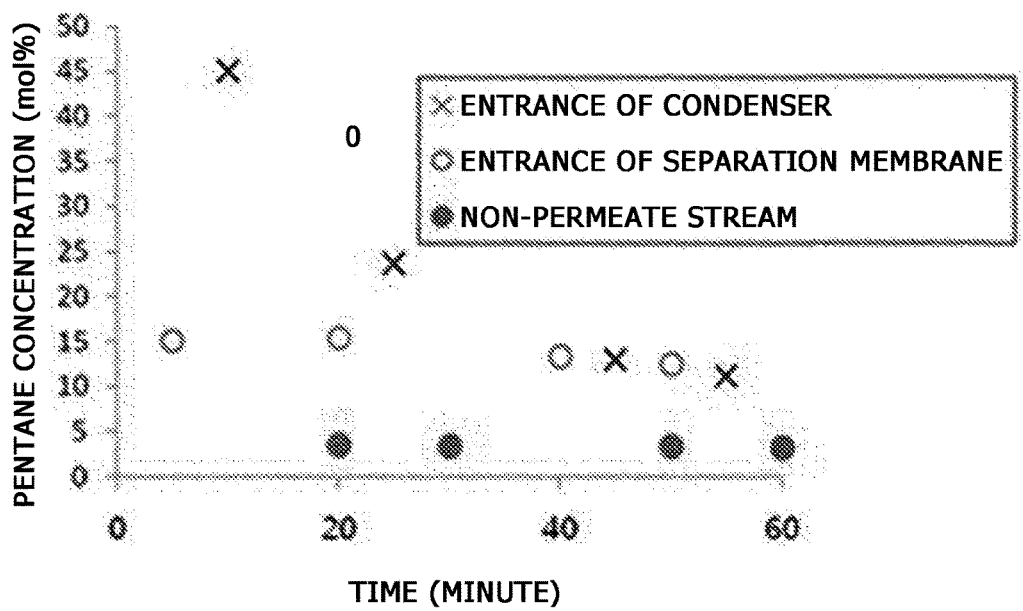
【Figure 12】
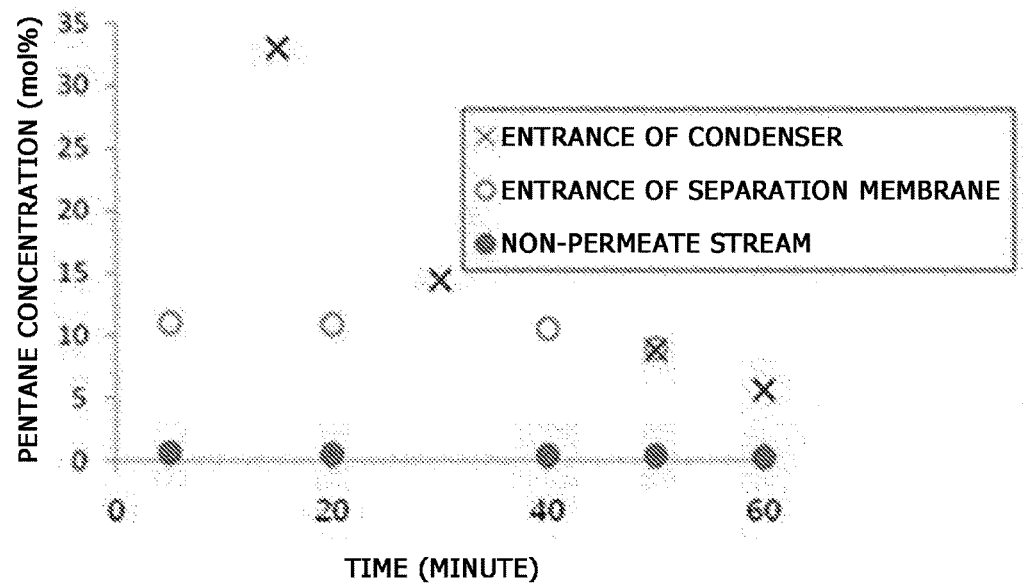

MEMBRANE SEPARATION DEVICE

This application is a National Stage Entry of International Application No. PCT/KR2014/001349, filed Feb. 19, 2014, and claims the benefit of Korean Application No. 10-2013-0017624, filed on Feb. 19, 2013, Korean Application No. 10-2013-0069800, filed on Jun. 18, 2013, and Korean Application No. 10-2013-0069799, filed on Jun. 18, 2013, all of which are hereby incorporated by reference in their entirety for all purposes as if fully set forth herein.

TECHNICAL FIELD

The present application relates to a membrane separation device, a membrane separation method, an apparatus for producing an expandable polystyrene, and a method for producing an expandable polystyrene.

BACKGROUND ART

Methods for selectively separating a certain gas from a gas mixture using a membrane are well known. Since a solution-diffusion model for gas separation membranes was proposed by T. Graham in the mid-1800s, research on gas separation membranes has been actively conducted, and the gas separation membranes has been commercially available and applied to various fields by the 1980s.

Generally, a gas permeation phenomenon in which gases pass through a non-porous membrane is explained using the solution-diffusion model proposed by T. Graham. In this case, respective gas components appear to have different relative diffusion coefficients and solubility constants according to materials constituting a membrane. Also, the most preferred materials for gas separation membranes are known to exhibit high permeability and high selectivity at the same time. Robeson (1991, J. Membr, Sci, 62, 165) found that, since there is a correlation between permeability and selectivity, the selectivity decreases when the permeability increases, whereas the permeability decreases when the selectivity increases, and thus proposed an upper limit in the correlation between the permeability and the selectivity. The fact that it is difficult to develop membrane materials exceeding the upper limit proposed by Robeson and it is far difficult to commercialize the membrane materials is known as one issue.

Therefore, methods of changing the conditions for a gas separation process, such as pressure difference, compositions, temperature and the like, have been used instead of developing a separation membrane exhibiting high permeability and high selectivity at the same time. However, since changing the conditions is changing process conditions, an increase in costs may be caused.

Meanwhile, in a process of producing an expandable polystyrene (hereinafter referred to as an "EPS"), an excessive amount of pentane that is a volatile organic compound (VOC) is introduced as a foaming agent into an EPS reactor so that the pentane is impregnated into polystyrene (PS) beads, and unimpregnated pentane is discharged out from the reactor. To prevent such discharged pentane from being discharged into the air, the discharged pentane is, for example, incinerated in a regenerative thermal oxidation (RTO) system, and then discharged into the air. In this process, however, a large amount of toxic gases such as carbon monoxide, carbon dioxide, or nitrogen oxides may be discharged into the air.

Since approximately 5 to 20% of the added foaming agent may be lost in this process, the manufacturing cost of the polystyrene may increase in an aspect of economic efficiency.

DISCLOSURE

Technical Problem

The present application is directed to providing a membrane separation device, a membrane separation method, an apparatus for producing an expandable polystyrene, and a method for producing an expandable polystyrene.

Technical Solution

A membrane separation device according to one exemplary embodiment of the present application includes different kinds of separation membranes coupled in series. For example, the membrane separation device includes two or more separation membranes, such as a first separation membrane, and a second separation membrane coupled to the first separation membrane. For example, the membrane separation device may include a first separation membrane having relatively high selectivity to a component to be separated from among a feed stream, and a second separation membrane coupled in series to a rear end of the first separation membrane and having relatively lower selectivity and relatively high permeability to the component be separated than the first separation membrane.

According to one exemplary embodiment, the membrane separation device may include a first separation membrane, into which a feed stream flows, and in which the feed stream is divided into a first permeate stream which passes through the first separation membrane and a first non-permeate stream which does not pass through the first separation membrane and is discharged, and a second separation membrane, into which the first non-permeate stream flows, and in which the first non-permeate stream is divided into a second permeate stream which passes through the second separation membrane and a second non-permeate stream which does not pass through the second separation membrane and is discharged. Also, the first separation membrane and the second separation membrane may have different selectivities and permeabilities, as described above.

The term "coupled in series" used herein means that the first separation membrane and the second separation membrane are coupled to discharge the permeate stream and the non-permeate stream as described above.

The term "selectivity" used herein refers to the degree in which a particular component from among two or more components is able to selectively pass through a separation membrane. Also, the term "permeability" used herein refers to a penetration rate in which a certain component passes through a separation membrane. For example, when it is assumed that, when a two-component mixture stream composed of a component A and a component B flow into a separation membrane device, the permeability of a component A is represented by $P_A$ and the permeability of a component B is represented by $P_B$, the permeability $P_A$ of the component A may be calculated by the following Equation 1.

$P_A$(GPU)=[permeation volume rate of component $A$ in mixture stream passing through separation membrane in standard state (i.e., standard temperature and pressure (STP))×$10^6$]/[area of separation membrane×difference in pressure between permeate stream and non-permeate stream]($cm^3/cm^2 \cdot s \cdot cmHg$)     [Equation 1]

In the foregoing, the term "standard state" refers to a state of a temperature of 0° C. and a pressure of 1 atm. Also, in the foregoing, the term "permeate stream" refers to a stream which passes through a separation membrane among streams flowing into the separation membrane, and the term "non-permeate stream" refers to a stream which does not pass through the separation membrane among stream flowing into the separation membrane.

Also, when the two-component mixture stream composed of the component A and the component B flows into the separation membrane device, the selectivity of the component A to the component B may be calculated by the following Equation 2.

$$\alpha_{AB}=P_A/P_B \qquad \text{[Equation 2]}$$

Generally, the capacity in a membrane separation process is associated with an area of a separation membrane, but the costs increase remarkably in proportion to the area in the case of the separation membrane. Also, since a separation membrane having high selectivity has poor permeability, the separation membrane having a wide area should be used. In the membrane separation device according to one exemplary embodiment of the present application, however, a separation membrane having a small area may also be used to separate a desired component to be separated with high efficiency by coupling different kinds of separation membranes having different selectivity and permeability to the component to be separated, for example, by coupling a separation membrane having relatively high selectivity to a front end and a separation membrane having relatively high permeability to a rear end in series, as described above. Therefore, the membrane separation device may have an effect of operating a process economically and efficiently.

Hereinafter, the membrane separation device according to one exemplary embodiment of the present application will be described in further detail with reference to the accompanying drawings. Also, in describing the present application, detailed descriptions with respect to known functions or constructions of the present application will be omitted for clarity. Also, the accompanying drawings are schematically shown to aid in understanding the present application, and thus parts irrelevant to the detailed description of the present application are omitted to describe the present application more clearly and definitively, and the scope of the present application is not limited by the accompanying drawings.

Hereinafter, a process of separating a gas mixture in the membrane separation device according to one exemplary embodiment of the present application will be described referring to FIG. 1. FIG. 1 is a schematic diagram showing a first embodiment of the exemplary membrane separation device. According to one exemplary embodiment, a first separation membrane device 10 and a second separation membrane device 20 of the membrane separation device 1 may include a first separation membrane 11 and a second separation membrane 21, both of which have different selectivities and permeabilities, respectively, as shown in FIG. 1.

According to one exemplary embodiment, the first separation membrane 11 and the second separation membrane 21 may satisfy the following Formula 1.

$$\alpha^1_{AB}-\alpha^2_{AB}>0 \qquad \text{[Formula 1]}$$

At the same time, the first separation membrane 11 and the second separation membrane 21 may also satisfy the following Formula 2.

$$P^2_A-P^1_A>0 \qquad \text{[Formula 2]}$$

In Formula 1, $\alpha^1_{AB}$ represents a selectivity ($P^1_A/P^1_B$) of a component A to a component B present in a feed stream flowing into the first separation membrane, and $\alpha^2_{AB}$ represents a selectivity ($P^2_A/P^2_B$) of the component A to the component B present in a first non-permeate stream flowing into the second separation membrane.

In the foregoing, $P^1_A$ and $P^1_B$ represent permeabilities of the component A and the component B present in the feed stream flowing into the first separation membrane, respectively, $P^2_A$ and $P^2_B$ represent permeabilities of the component A and the component B present in the first non-permeate stream flowing into the second separation membrane, respectively.

In the foregoing, the component A represents a component to be separated from among at least two components flowing into each separation membrane, and the component B represents the other component with the exception of the component A from among the at least two components flowing into each separation membrane.

Also, in the membrane separation device described below, the parameters $\alpha^1_{AB}$, $\alpha^2_{AB}$, $P^1_A$, $P^1_B$, $P^2_A$ and $P^2_B$ are as described above.

In the present application, a component to be separated may be recovered with high efficiency when the separation membranes 11 and 21 are coupled in series to satisfy Formulas 1 and 2. Also, since a separation membrane having a small cross-sectional area may be used to separate the component to be separated with high efficiency, compared to when the membrane separation device is composed of only one first separation membrane having high selectivity, a process of separating a gas mixture may be performed in a more economic manner.

For example, when a feed stream $F_1$ flows into the first separation membrane device 10 according to one exemplary embodiment of the present application, as shown in FIG. 1, the feed stream $F_1$ may be divided into a first permeate stream $F_3$ which passes through the first separation membrane 11, and a first non-permeate stream $F_2$ which does not pass through the first separation membrane 11 and is discharged to flow into the second separation membrane device 20. In this case, since the first permeate stream $F_3$ passes through the first separation membrane 11 having relatively much higher selectivity and lower permeability to the component A than the second separation membrane 21, the first permeate stream $F_3$ may be a stream in which component A is densely included relatively. Also, the first non-permeate stream $F_2$ flows into the second separation membrane device 20, and then may be divided into a second permeate stream $F_5$ which passes through the second separation membrane 21, and a second non-permeate stream $F_4$ which does not pass through the second separation membrane 21 and is discharged. In this case, since the second permeate stream $F_5$ passes through the second separation membrane 21 having relatively lower selectivity and higher permeability than the first separation membrane 11, the second permeate stream $F_5$ may be a stream in which component A is densely included relatively although the component A is present in a smaller quantity than that of the first permeate stream $F_3$. As a result, the component A may also be hardly included in the second non-permeate stream $F_4$ finally flowing out by means of this process. In the foregoing, the term "stream in which component is densely included" used herein refers to a stream in which respective components to be separated in the first permeate stream $F_3$ or the second permeate stream $F_5$ have higher contents than at least one or more components to be separated in the feed stream $F_1$. For example, the term "stream in which component is densely included" may refer to a stream in which each of the components to be separated in the first permeate stream $F_3$ or the second permeate stream $F_5$ has a content of 50% by weight or more, 80% by weight or more, 90% by weight or more, 95% by weight or more, or 99% by weight or more.

Also, the membrane separation device 1 includes the first separation membrane 11 and the second separation membrane 21 satisfying Formulas 1 and 2. At the same time, the membrane separation device 1 may preferably include the first and second separation membranes 11 and 21 having a selectivity of 1 or more to a material to be separated, especially a component to be separated. For example, when the feed stream $F_1$ including the component A and the component B with the exception of the component A from among at least two components passing through each separation membrane flows into the membrane separation device 1 as shown in FIG. 1, the selectivity ($\alpha^1_{AB}$) of the component A to the component B in the first separation membrane 11, and the selectivity ($\alpha^2_{AB}$) of the component A to the component B in the second separation membrane 21 may satisfy the following Formulas 3 and 4.

$$\alpha^1_{AB} > 1 \quad \text{[Formula 3]}$$

$$\alpha^2_{AB} > 1 \quad \text{[Formula 4]}$$

In the membrane separation device 1, the component to be separated may be separated and recovered with high selectivity when the selectivity ($\alpha^1_{AB}$) of the component A to the component B in the first separation membrane 11, and the selectivity ($\alpha^2_{AB}$) of the component A to the component B in the second separation membrane 21 satisfy the following Formulas 3 and 4.

Preferably, the first separation membrane 11 and the second separation membrane 21 included in the membrane separation device 1 may also satisfy Formulas 1 and 2, and the permeability ($P^1_B$) of the component B in the first separation membrane 11 and the permeability ($P^2_B$) of the component B in the second separation membrane 21 may also satisfy the following Formula 5 at the same time.

$$P^2_B - P^1_B > 0 \quad \text{[Formula 5]}$$

For example, when it is assumed that $P^1_A$ and $P^1_B$ of the first separation membrane 11 of the membrane separation device 1 are 20 and 2, respectively, and $P^2_A$ and $P^2_B$ of the second separation membrane 21 are 40 and 10, respectively, an $\alpha^1_{AB}$ value of the first separation membrane 11 becomes 10, and an $\alpha^2_{AB}$ value of the second separation membrane 21 becomes 4. Therefore, a value of $\alpha^1_{AB} - \alpha^2_{AB}$ becomes 6, which satisfies Formula 1. Also, a value of $P^2_A - P^1_A$ becomes 20, which satisfies Formula 2. In this case, both of $\alpha^1$ and $\alpha^2_{AB}$ have values higher than 1 as given in Formulas 3 and 4, and a value of $P^2_B - P^1_B$ becomes 8, which also satisfies Formula 5.

The separation membranes 11 and 21 which may be included in the separation membrane devices 10 and 20 used in the membrane separation device 1 according to one exemplary embodiment of the present application may be used without particular limitation as long as they satisfy Formulas 1 and 2. For example, the separation membranes 11 and 21 may be selected from various types of known separation membranes according to a volatile organic compound (VOC) component to be separated, and may be used without limitation.

Also, when the separation membranes 11 and 21 satisfy Formulas 1 and 2 as described above, the permeability ($P^1_A$) of the first separation membrane 11 included in the first separation membrane device 10, and the permeability ($P^2_A$) of the second separation membrane 21 included in the second separation membrane device 20 may be 20 GPU or more, for example, 30 GPU or more, 40 GPU or more, preferably 50 GPU or more, and more preferably 100 GPU or more, but the present application is not particularly limited thereto. When the permeability ($P^1_A$) of the first separation membrane 11 and the permeability ($P^2_A$) of the second separation membrane 21 are less than 20 GPU, the processing capacity of the separation membrane may be degraded. An upper limit of the permeability may, for example, less than or equal to 100,000 GPU in consideration of actual applicability, but the present application is not particularly limited thereto.

According to one exemplary embodiment, when the separation membranes 11 and 21 satisfy Formulas 1 and 2 as described above, the selectivity ($\alpha^1_{AB}$) of the component A to the component B in the first separation membrane 11, and the selectivity ($\alpha^2_{AB}$) of the component A to the component B in the second separation membrane 21 may be 10 or more, for example, 15 or more, preferably 20 or more, and more preferably 30 or more, but the present application is not particularly limited thereto. When the selectivity ($\alpha^1_{AB}$) of the component A to the component B in the first separation membrane 11, and the selectivity ($\alpha^2_{AB}$) of the component A to the component B in the second separation membrane 21 is less than 10, separation efficiency may be degraded.

According to one exemplary embodiment, the membrane separation device 1 may include a vacuum pump 40. The vacuum pump 40 may include the membrane separation device according to one exemplary embodiment of the present application to provide a different in pressure between the first and second permeate streams and the first and second non-permeate streams passing through the first separation membrane 11 and the second separation membrane 21, respectively. Also, although not shown, the membrane separation device 1 may include a pressure device configured to control a pressure of a stream flowing into the first separation membrane 11 before the feed stream flows into the first separation membrane 11, for example, a compressor. An increase in pressure of the feed stream may be caused by the pressure device, and thus a difference in pressure between the first and second permeate streams and the first and second non-permeate streams passing through the first separation membrane 11 and the second separation membrane 21, respectively, may be provided.

FIG. 2 is a schematic diagram showing a second embodiment of the membrane separation device according to the present application.

As shown in FIG. 2, the exemplary membrane separation device includes a condenser 2 into which a feed stream including at least two components flows, a first separation membrane 11, into which an uncondensed stream from the condenser flows, and in which the uncondensed stream is divided into a first permeate stream $F_3$ which passes through the first separation membrane and a first non-permeate stream $F_2$ which does not pass through the first separation membrane and is discharged, and a second separation membrane 21, into which the first non-permeate stream $F_2$ flows, and in which the first non-permeate stream is divided into a second permeate stream $F_5$ which passes through the second separation membrane and a second non-permeate stream $F_4$ which does not pass through the second separation membrane and is discharged. Also, the first separation membrane 11 and the second separation membrane 21 may have different selectivities and permeabilities.

The first separation membrane 11 and the second separation membrane 21 may satisfy Formula 1 to 5 as described above in the membrane separation device, and thus have the same effects as described above.

According to one exemplary embodiment, the membrane separation device 1 may include a condenser 2, as shown in FIG. 2. When the feed stream $F_1$ passes through the condenser 2 before flowing into the first separation membrane 11, a condensable component $F_7$ among the components to be separated may be condensed to be separated in advance. Then, only a mixed gas in a mixture of an uncondensable gas and a component to be separated in an uncondensed gas state may flow into the first separation membrane 11, thereby reducing an area of membranes used.

FIG. 3 is a schematic diagram showing a third embodiment of the membrane separation device according to the present application.

As shown in FIG. 3, the exemplary membrane separation device includes a first separation membrane 11, into which a feed stream flows, and in which the feed stream is divided into a first permeate stream $F_3$ which passes through the first separation membrane and a first non-permeate stream $F_2$ which does not pass through the first separation membrane and is discharged, a second separation membrane 21, into which the first non-permeate stream $F_2$ flows, and in which the first non-permeate stream is divided into a second permeate stream $F_5$ which passes through the second separation membrane and a second non-permeate stream $F_4$ which does not pass through the second separation membrane and is discharged, and a gas-liquid separator 30 coupled to a front end of the first separation membrane 11 and/or coupled between the first separation membrane 11 and the second separation membrane 21 to divide the first permeate stream $F_3$ and the second permeate stream $F_5$ into a gas stream $F_6$ and a liquid stream, discharge the divided gas stream and allow the gas stream $F_6$ to flow into the first separation membrane 11 and/or second separation membrane 21 together with the feed stream $F_1$ or the first non-permeate stream $F_2$. Also, the first separation membrane 11 and the second separation membrane 21 may have different selectivity and permeability.

The first separation membrane 11 and the second separation membrane 21 may satisfy Formulas 1 to 5 as described above in the membrane separation device, and thus have the same effects as described above.

According to one exemplary embodiment, the membrane separation device 1 may include a gas-liquid separator 30, as shown in FIG. 3. The first permeate stream $F_3$ and the second permeate stream $F_5$ in the membrane separation device 1 may flow into the gas-liquid separator 30, and the components included in the first permeate stream $F_3$ and the second permeate stream $F_5$ are gas-liquid separated in the gas-liquid separator 30, and the separated gas stream $F_6$ may again flow into the first separation membrane 11 and/or the second separation membrane 21 to be divided again. For example, when the membrane separation device 1 according to one exemplary embodiment of the present application includes the gas-liquid separator 30, the separated gas stream $F_6$ may be re-used in the membrane separation process to maximize an amount of the components recovered in this process.

According to one exemplary embodiment, although not shown, the membrane separation device may further include a pressure regulator, for example, a pressure or decompression device.

For example, the gas-liquid separator may further include a pressure device configured to apply a pressure to the gas stream $F_6$ before the gas stream $F_6$ flows into the first separation membrane 11. According to one exemplary embodiment, the pressure device may be a compressor, but the present application is not limited thereto. The feed stream $F_1$ flowing into the first separation membrane 11 and the first non-permeate stream $F_2$ flowing into the second separation membrane 21 may be high-pressure streams having a higher pressure condition than the gas stream $F_6$ having a normal pressure, and thus the pressure of the gas stream $F_6$ having a normal pressure may be adjusted to the same pressure as the feed stream $F_1$ and/or the first non-permeate stream $F_2$ by means of the pressure device before the gas stream $F_6$ is mixed with the feed stream $F_1$ fed into the first separation membrane 11 and the first non-permeate stream $F_2$ flowing into the second separation membrane 21.

According to one exemplary embodiment, the pressure regulator may also be a decompression device. For example, the membrane separation device 1 may further include a decompression device configured to decompress the first non-permeate stream $F_2$, for example, a control valve installed at a pipe through which the first non-permeate stream $F_2$ flows. In this case, the gas-liquid separator 30 may be coupled so that the gas stream $F_6$ discharged from the gas-liquid separator 30 flows into the second separation membrane 21, as shown in FIG. 3. Since the above-described pressure device should be separately installed to allow the gas stream $F_6$ having the normal pressure to flow into the first separation membrane 11, additional costs may occur. As described above, however, the separated gas stream $F_6$ may be re-used in the membrane separation process without installing an additional pressure device by adjusting a pressure of the first non-permeate stream $F_2$ to a normal pressure by means of the decompression device, thereby maximizing an amount of the components recovered in this process.

FIG. 4 is a schematic diagram showing a fourth embodiment of the membrane separation device according to the present application.

As shown in FIG. 4, the exemplary membrane separation device includes a condenser 2 into which a feed stream including at least two components flows, a first separation membrane 11, into which an uncondensed stream from the condenser flows, and in which the uncondensed stream is divided into a first permeate stream $F_3$ which passes through the first separation membrane and a first non-permeate stream $F_2$ which does not pass through the first separation membrane and is discharged, a second separation membrane 21, into which the first non-permeate stream $F_2$ flows, and in which the first non-permeate stream is divided into a second permeate stream $F_5$ which passes through the second separation membrane and a second non-permeate stream $F_4$ which does not pass through the second separation membrane and is discharged, and a gas-liquid separator 30 coupled to a front end of the first separation membrane 11 and/or coupled between the first separation membrane 11 and the second separation membrane 21 to divide the first permeate stream $F_3$ and the second permeate stream $F_5$ into a gas stream $F_6$ and a liquid stream, discharge the divided gas stream and allow the gas stream $F_6$ to flow into the first separation membrane 11 and/or second separation membrane 21 together with the feed stream $F_1$ or the first non-permeate stream $F_2$. Also, the first separation membrane 11 and the second separation membrane 21 may have different selectivities and permeabilities.

The first separation membrane 11 and the second separation membrane 21 may satisfy Formulas 1 to 5 as described above in the membrane separation device, and thus have the same effects as described above.

According to one exemplary embodiment, as shown in FIG. 4, the membrane separation device 1 may include a condenser 2, a gas-liquid separator 30, and a pressure regulator, and thus have the same effects as described above.

The membrane separation device according to one exemplary embodiment of the present application may be used for a variety of separating processes, and may, for example, be used for a process for producing an expandable polystyrene (EPS).

When the membrane separation device 1 according to one exemplary embodiment of the present application is used in a process system for producing an EPS, pentane used as foaming agent upon EPS production may be separated and recovered with low costs, thereby realizing an environmentally friendly EPS producing process. Also, the separated VOC may be recycled and re-used in the EPS producing process, thereby reducing the production cost.

According to one exemplary embodiment, the process system for producing an EPS may include a reactor in addition to the membrane separation device 1.

According to one exemplary embodiment, polystyrene beads may, for example, be polymerized in the reactor, and the reactor may also be a column filled with a VOC that is an expandable gas (for example, pentane gas).

The expandable gas comes in contact with the polystyrene beads to be impregnated in the polystyrene beads, and an unimpregnated expandable gas may be discharged through a discharge device to be described below from the reactor together with an uncondensable gas as will be described below.

According to one exemplary embodiment, an uncondensable gas feeding device configured to feed an uncondensable gas may also be coupled to the reactor, and the uncondensable gas fed from the uncondensable gas feeding device may be discharged from the reactor together with the unimpregnated expandable gas to flow into the membrane separation device. For example, the unimpregnated expandable gas and the uncondensable gas may be discharged through the discharge device coupled to one side rather than the other side of the reactor to which the uncondensable gas feeding device is coupled. For example, the gas stream $F_1$ discharged from the discharge device may be the feed stream $F_1$ flowing in the above-described membrane separation device 1.

According to one exemplary embodiment, the process system for producing an EPS may further include a condenser 2, a distillation apparatus, an adsorber, an absorber, or a gas-liquid separator 30 in addition to the membrane separation device 1, the EPS reactor, the uncondensable feeding device, and the discharge device. For example, the condenser 2 may be coupled to the discharge device so that the gas discharged from the discharge device flows in the condenser 2. When the feed stream passes through the condenser before the feed stream flows into the first separation membrane 11, a condensable component among the components to be separated may be condensed and separated in advance. Only a mixed gas in a mixture of the uncondensable gas and the component in an uncondensed gas state may flow into the first separation membrane 11, thereby reducing an area of membranes used.

Also, the exemplary process system for producing an EPS may further include an RTO system. The process system for producing an EPS according to one exemplary embodiment of the present application may include the RTO system as a combustion device configured to prevent residual VOC components remaining after passing through the membrane separation device from being emitted into the air.

The present application is directed to providing an apparatus for producing an expandable polystyrene (EPS).

The apparatus for producing an EPS according to one exemplary embodiment of the present application includes a reactor, an uncondensable gas feeding device and a discharge device, both of which are coupled to the reactor, and a separation membrane coupled to the discharge device. For example, when a mixed gas obtained by mixing an unimpregnated expandable gas with an uncondensable gas and an expandable polystyrene (hereinafter referred to as an "EPS") discharged from the discharge device passes through the separation membrane, pentane used as a foaming agent upon EPS production may be separated and recovered with low costs, thereby realizing an environmentally friendly EPS producing process. Also, the separated expandable gas may be recycled and re-used in the EPS producing process, thereby reducing the production cost.

FIG. 5 is a diagram showing one exemplary embodiment of the apparatus for producing an EPS according to the present application.

As shown in FIG. 5, the apparatus for producing an EPS according to one exemplary embodiment of the present application may include a reactor 2, an uncondensable gas feeding device 3, a discharge device 4, and a separation membrane 1.

In the foregoing, the reactor 2 is a reactor in which a polystyrene bead is polymerized. In this case, the reactor may be filled with a styrene-based monomer and a polymerization initiator, both of which are used to polymerize the polystyrene bead. Also, the reactor may be further filled with at least one additive selected from the group consisting of a molecular weight modifier, a flame retardant, a dispersing agent, a dispersing aid, a pH control agent, and a surfactant, all of which are required for polymerization, when necessary.

According to one exemplary embodiment, the polystyrene bead may be polymerized using various polymerization methods known in the related art, but the present application is not particularly limited thereto. For example, the polystyrene bead may be polymerized using a suspension polymerization method.

Also, the reactor 2 may be filled with an expandable gas to expand the polystyrene bead after the polystyrene bead is polymerized in the reactor. The expandable gas is impregnate in the polystyrene bead, and a portion of the expandable gas may remain inside the reactor in a state in which the expandable gas is not impregnated in the polystyrene bead.

According to one exemplary embodiment, various types of expandable gases are known as the expandable gas in the related art, but the present application is not particularly limited thereto. For example, a volatile organic compound, for example, pentane gas, may be used as the expandable gas.

As shown in FIG. 5, the exemplary apparatus for producing an EPS may also include an uncondensable gas feeding device 3. The uncondensable gas feeding device 3 is a device configured to feed the uncondensable gas to the reactor 2, and is coupled to one side of the reactor 2. As the uncondensable gas is fed to the reactor 2, condensation of the unimpregnated expandable gas may be prevented, thereby easily discharging the expandable gas, which is not impregnated in the polystyrene bead, from the reactor 2.

Various types of uncondensable gases known in the related art may be used as the uncondensable gas without limitation. For example, nitrogen may be used as the uncondensable gas As shown in FIG. 5, the apparatus for producing an EPS may also include a discharge device 4 configured to discharge a mixed gas including the expandable gas, which is not impregnated in the polystyrene bead polymerized in the reactor 2, and the uncondensable gas. The unimpregnated expandable gas and the uncondensable gas may be discharged through the discharge device 4 of the reactor 2. For example, the mixed gas stream $F_1$ discharged from the discharge device may be a feed stream $F_1$ flowing into a separation membrane 1 as will be described below. For example, the discharge device 4 may be coupled to one side rather than the other side of the reactor to which the uncondensable gas feeding device 3 is coupled, as shown in FIG. 5.

According to one exemplary embodiment, the apparatus for producing an EPS according to one exemplary embodiment of the present application may also include a separation membrane 1 coupled to allow the mixed gas stream discharged from the discharge device 4 to flows therein. In the apparatus for producing an EPS according to one exemplary embodiment of the present application, as the mixed gas stream including the unimpregnated expandable gas components passes through the separation membrane 1, the unimpregnated expandable gas may be separated, and the separated expandable gas may be re-used to produce the EPS, thereby economically producing the EPS and preventing environmental pollution.

The separation membrane 1 may, for example, be coupled to the discharge device 4 to allow the mixed gas stream to flow into the discharge device 4, and the mixed gas stream flowing into the separation membrane 1 may be divided into a permeate stream which passes through the separation membrane, and a non-permeate stream which does not pass through the separation membrane. The permeate stream passing through the separation membrane may be a stream having a relatively higher expandable gas concentration than the mixed gas stream.

According to one exemplary embodiment, as shown in FIG. 5, the separation membrane included in the apparatus for producing an EPS includes two or more separation membranes, like the second separation membrane 21 coupled to the first separation membrane 11. For example, the apparatus for producing an EPS may include a first separation membrane 11 having relatively high selectivity to an expandable gas component to be separated such as pentane in the feed stream such as the mixed gas discharged from the EPS reactor, and a second separation membrane 21 coupled in series to a rear end of the first separation membrane 11 and having relatively lower selectivity and higher permeability to the expandable gas component than the first separation membrane 11.

Also, the apparatus for producing an EPS may include the first separation membrane 11, into which a gas stream flows, and in which the gas stream is divided into a first permeate stream $F_3$ which passes through the first separation membrane and a first non-permeate stream $F_2$ which does not pass through the first separation membrane and is discharged, and the second separation membrane 21, into which the first non-permeate stream $F_2$ flows, and in which the first non-permeate stream is divided into a second permeate stream $F_5$ which passes through the second separation membrane and a second non-permeate stream $F_4$ which does not pass through the second separation membrane and is discharged, as shown in FIG. 5. Also, the first separation membrane 11 and the second separation membrane 21 may have different selectivity and permeability, as described above.

According to one exemplary embodiment, the first separation membrane 11 and the second separation membrane 21 may satisfy the following Formula 1.

$$\alpha^1_{AB} - \alpha^2_{AB} > 0 \quad \text{[Formula 1]}$$

At the same time, the first separation membrane 11 and the second separation membrane 21 may also satisfy the following Formula 2.

$$P^2_A - P^1_A > 0 \quad \text{[Formula 2]}$$

In the Formula 1, $\alpha^1_{AB}$ represents a selectivity ($P^1_A/P^1_B$) of a component A to a component B present in the mixed gas stream $F_1$ flowing into the first separation membrane, and $\alpha^2_{AB}$ represents a selectivity ($P^2_A/P^2_B$) of the component A to the component B present in the first non-permeate stream $F_2$ flowing into the second separation membrane.

In the foregoing, $P^1_A$ and $P^1_B$ represent permeabilities of the component A and the component B present in the mixed gas stream $F_1$ flowing into the first separation membrane, respectively, and $P^2_A$ and $P^2_B$ represent permeabilities of the component A and the component B present in the first non-permeate stream $F_2$ flowing into the second separation membrane, respectively, In the foregoing, the component A represents at least one component to be separated from at least two components flowing into each separation membrane, for example, a VOC component, and the component B represents the other component with the exception of the component A in the at least two components flowing into each separation membrane.

For the apparatus for producing an EPS, the following parameters $\alpha^1_{AB}$, $\alpha^2_{AB}$, $P^1_A$, $P^1_B$, $P^2_A$ and $P^2_B$ are also as defined above.

In the present application, when the separation membranes 11 and 21 are coupled in series to satisfy Formulas 1 and 2, the expandable gas, for example, a VOC component, may be recovered with high efficiency, and the separation membrane having a small cross-sectional area may also be used to separate the expandable gas with a high recovery rate, compared to when the membrane separation device is composed of only one first separation membrane having high selectivity. Therefore, it is possible to perform a process for separating the expandable gas more economically.

For example, as shown in FIG. 5, when the feed stream $F_1$ flows in the first separation membrane device 10 according to one exemplary embodiment of the present application, the feed stream $F_1$ may be divided into a first permeate stream $F_3$ which passes through the first separation membrane 11, and a first non-permeate stream $F_2$ which is discharged without passing through the first separation membrane 11 and flows into the second separation membrane device 20. In this case, since the first permeate stream $F_3$ passes through the first separation membrane 11 having relatively higher selectivity and lower permeability to the component A than the second separation membrane 21, the first permeate stream $F_3$ may be a stream in which component A is densely included relatively. Also, the first non-permeate stream $F_2$ flows into the second separation membrane device 20, and may be then divided into a second permeate stream $F_5$ which passes through the second separation membrane 21, and a second non-permeate stream $F_4$ which is discharged without passing through the second separation membrane 21. In this case, since the second permeate stream $F_5$ passes through the second separation membrane 21 having relatively lower selectivity and higher permeability than the first separation membrane 11, the second permeate stream $F_5$ may be a stream in which component A is densely included relatively although the component A is present in a smaller quantity than that of the first permeate stream $F_3$. As a result, the component A may also be hardly included in the second non-permeate stream $F_4$ finally flowing out by means of this process.

Also, the separation membrane 1 includes the first separation membrane 11 and the second separation membrane 21, both of which satisfy Formulas 1 and 2. At the same time, the separation membrane 1 may preferably include the separation membranes 11 and 21 having a selectivity of more than 1 to a material to be separated, especially an expandable gas. For example, as shown in FIG. 5, when the feed stream $F_1$ including an expandable gas component A and a component B with the exception of the component A in at least two components flowing into each separation membrane flows into the separation membrane 1, the selectivity ($\alpha^1_{AB}$) of the component A to the component B in the first separation membrane 11, and the selectivity ($\alpha^2_{AB}$) of the component A to the component B in the second separation membrane 21 may satisfy the following Formulas 3 and 4.

$$\alpha^1_{AB} > 1 \quad \text{[Formula 3]}$$

$$\alpha^2_{AB} > 1 \quad \text{[Formula 4]}$$

In the membrane separation device 1, when the selectivity ($\alpha^1_{AB}$) of the component A to the component B in the first separation membrane 11, and the selectivity ($\alpha^2_{AB}$) of the component A to the component B in the second separation membrane 21 satisfy Formulas 3 and 4, the expandable gas, for example, a VOC, may be separated and recovered with high selectivity.

Preferably, the first separation membrane 11 and the second separation membrane 21 included in the membrane separation device 1 may also satisfy Formulas 1 and 2, and the permeability ($P^1_B$) of the component B in the first separation membrane 11 and the permeability ($P^2_B$) of the component B in the second separation membrane 21 may also satisfy the following Formula 5 at the same time.

$$P^2_B - P^1_B > 0 \quad \text{[Formula 5]}$$

For example, when it is assumed that $P^1_A$ and $P^1_B$ of the first separation membrane 11 of the membrane separation device 1 are 20 and 2, respectively, and $P^2_A$ and $P^2_B$ of the second separation membrane 21 are 40 and 10, respectively, an $\alpha^1_{AB}$ value of the first separation membrane 11 becomes 10, and an $\alpha^2_{AB}$ value of the second separation membrane 21 becomes 4. Therefore, a value of $\alpha^1_{AB} - \alpha^2_{AB}$ becomes 6, which satisfies Formula 1. Also, a value of $P^2_A - P^1_A$ becomes 20, which satisfies Formula 2. In this case, both of $\alpha^1_{AB}$ and $\alpha^2_{AB}$ have values higher than 1 as given in Formulas 3 and 4, and a value of $P^2_B - P^1_B$ becomes 8, which also satisfies Formula 5.

When the separation membranes 11 and 21 which may be included in the separation membrane devices 10 and 20 used in the separation membrane 1 according to one exemplary embodiment of the present application satisfy Formulas 1 and 2, various types of separation membranes are selected and used without limitation according to a VOC component to be separated, but the present application is not particularly limited thereto.

Also, the separation membranes 11 and 21 may be used without particular limitation as long as they satisfy Formulas 1 and 2 as described above. The permeability ($P^1_A$) of the first separation membrane 11 included in the first separation membrane device 10 and the permeability ($P^2_A$) of the second separation membrane 21 included in the second separation membrane device 20 may be 20 GPU or more, for example, 30 GPU or more, 40 GPU or more, preferably 50 GPU or more, and more preferably 100 GPU or more. When the permeability ($P^1_A$) of the first separation membrane 11 and the permeability ($P^2_A$) of the second separation membrane 21 is less than 20 GPU, the processing capacity of the separation membrane may be degraded. An upper limit of the permeability may, for example, less than or equal to 100,000 GPU in consideration of actual applicability, but the present application is not particularly limited thereto.

According to one exemplary embodiment, the separation membranes 11 and 21 may be used without particular limitation as long as they satisfy Formulas 1 and 2 as described above. For example, the selectivity ($\alpha^1_{AB}$) of the component A to the component B in the first separation membrane 11 and the selectivity ($\alpha^2_{AB}$) of the component A of the component B in the second separation membrane 21 may be 10 or more, for example, 15 or more, preferably 20 or more, and more preferably 30 or more. When the selectivity ($\alpha^1_{AB}$) of the component A to the component B in the first separation membrane 11 and the selectivity ($\alpha^2_{AB}$) of the component A to the component B in the second separation membrane 21 is less than 10, separation efficiency may be degraded.

According to one exemplary embodiment, the apparatus for producing an EPS may include a vacuum pump 40. The vacuum pump 40 may be included in the apparatus for producing an EPS according to one exemplary embodiment of the present application to provide a difference in pressure between the first and second permeate streams and the first and second non-permeate streams passing respectively through the first separation membrane 11 and the second separation membrane 21. Although not shown, the membrane separation device 1 may also further include a pressure device configured to adjust a pressure of a stream flowing into the first separation membrane before the feed stream flows into the first separation membrane 11, for example, a compressor. A pressure may be applied to the feed stream by the pressure device, thereby providing a difference in pressure to the first and second permeate streams and the first and second non-permeate streams passing respectively through the first separation membrane 11 and the second separation membrane 21.

FIG. 6 is a schematic diagram showing another exemplary embodiment of the apparatus for producing an EPS according to the present application.

As shown in FIG. 6, the exemplary apparatus for producing an EPS includes a reactor 2, an uncondensable gas feeding device 3 configured to feed an uncondensable gas to the reactor 2, a discharge device 4 coupled to the reactor 2, a condenser 5 coupled to the discharge device 4, and a separation membrane 1 into which an uncondensed stream from the condenser flows. According to one exemplary embodiment, the separation membrane 1 may include a first separation membrane and a second separation membrane, as described above. For example, the separation membrane 1 may include the first separation membrane 11, into which an uncondensed stream from the condenser 5 flows, and in which the uncondensed stream is divided into a first permeate stream $F_3$ which passes through the first separation membrane and a first non-permeate stream $F_2$ which does not pass through the first separation membrane and is discharged, and the second separation membrane 21, into which the first non-permeate stream $F_2$ flows, and in which the first non-permeate stream is divided into a second permeate stream $F_5$ which passes through the second separation membrane and a second non-permeate stream $F_4$ which does not pass through the second separation membrane and is discharged. As described above, the first separation membrane 11 and the second separation membrane 21 may have different selectivities and permeabilities. Also, the first separation membrane 11 and the second separation membrane 21 may satisfy Formula 1 to 5 as described above in the first embodiment of the apparatus for producing an EPS, and thus have the same effects as described above.

According to one exemplary embodiment, as shown in FIG. 6, the condenser 5 may be coupled to the discharge device 4 so that the mixed gas discharged from the discharge device 4 flows in the condenser 5. When the apparatus for producing an EPS according to one exemplary embodiment of the present application includes the condenser 5, the feed stream $F_1$ passes through the condenser 5 before the feed stream $F_1$ flows into the first separation membrane 11. As a result, a component to be separated, that is, a condensable component $F_7$ in the expandable gas, may be condensed, and separated in advance. Only a mixed gas in a mixture of the uncondensed expandable gas component and the uncondensable gas may flow into the first separation membrane 11, thereby reducing an area of membranes used.

FIG. 7 is a schematic diagram showing still another exemplary embodiment of the apparatus for producing an EPS according to the present application.

As shown in FIG. 7, the exemplary apparatus for producing an EPS includes a reactor 2, an uncondensable gas feeding device 3 configured to feed an uncondensable gas to the reactor 2, a discharge device 4 coupled to the reactor 2, and a separation membrane 1 coupled to the discharge device 4, and further includes a gas-liquid separator 30 coupled to the separation membrane 1.

According to one exemplary embodiment, the separation membrane 1 may include a first separation membrane 11 and a second separation membrane 21, as described above. For example, the separation membrane 1 may include the first separation membrane 11, into which a mixed gas stream discharged from the discharge device 4 flows, and in which the mixed gas stream is divided into a first permeate stream $F_3$ which passes through the first separation membrane and a first non-permeate stream $F_2$ which does not pass through the first separation membrane and is discharged, and the second separation membrane 21, into which the first non-permeate stream $F_2$ flows, and in which the first non-permeate stream is divided into a second permeate stream $F_5$ which passes through the second separation membrane and a second non-permeate stream $F_4$ which does not pass through the second separation membrane and is discharged. As described above, the first separation membrane 11 and the second separation membrane 21 may have different selectivity and permeability. Also, the first separation membrane 11 and the second separation membrane 21 may satisfy Formulas 1 to 5 as described above in the first embodiment of the apparatus for producing an EPS, and thus have the same effects as described above.

According to one exemplary embodiment, as shown in FIG. 7, the apparatus for producing an EPS may include a gas-liquid separator 30. The first permeate stream $F_3$ and the second permeate stream $F_5$ in the membrane separation device 1 may flow in the gas-liquid separator 30, and the components included in the first permeate stream $F_3$ and the second permeate stream $F_5$ are gas-liquid separated in the gas-liquid separator 30, and the separated gas stream $F_6$ may again flow into the first separation membrane 11 and/or the second separation membrane 21 to be divided again. For example, when the apparatus for producing an EPS according to one exemplary embodiment of the present application includes the gas-liquid separator 30, the separated gas stream may be re-used in the membrane separation process to maximize an amount of the components recovered in this process.

According to one exemplary embodiment, although not shown, the apparatus for producing an EPS may further include a pressure regulator, for example, a pressure or decompression device.

For example, the gas-liquid separator 30 may further include a pressure device configured to apply a pressure to the gas stream $F_6$ before the gas stream $F_6$ flows into the first separation membrane 11. According to one exemplary embodiment, the pressure device may be a compressor, but the present application is not limited thereto. The feed stream $F_1$ flowing into the first separation membrane 11 and the first non-permeate stream $F_2$ flowing into the second separation membrane 21 may be high-pressure streams having a higher pressure condition than the gas stream $F_6$ having a normal pressure, and thus the pressure of the gas stream $F_6$ having a normal pressure may be adjusted to the same pressure as the feed stream $F_1$ and/or the first non-permeate stream $F_2$ by means of the pressure device before the gas stream $F_6$ is mixed with the feed stream $F_1$ fed through the first separation membrane 11 and the first non-permeate stream $F_2$ flowing into the second separation membrane 21.

According to one exemplary embodiment, the pressure regulator may also be a decompression device. For example, the membrane separation device 1 may further include a decompression device configured to decompress the first non-permeate stream $F_2$, for example, a control valve installed at a pipe through which the first non-permeate stream $F_2$ flows. In this case, the gas-liquid separator 30 may be coupled so that the gas stream $F_6$ discharged from the gas-liquid separator 30 flows into the second separation membrane 21, as shown in FIG. 7. Since the above-described pressure device should be separately installed to allow the gas stream $F_6$ having the normal pressure to flow into the first separation membrane 11, additional costs may occur. As described above, however, the separated gas stream $F_6$ may be re-used in the membrane separation process without installing an additional pressure device by adjusting a pressure of the first non-permeate stream $F_2$ to a normal pressure by means of the decompression device, thereby maximizing an amount of the components recovered in this process. In the foregoing, the term "normal pressure" refers to an atmospheric pressure, for example, 1 atm.

FIG. 8 is a schematic diagram showing yet another exemplary embodiment of the apparatus for producing an EPS according to the present application.

As shown in FIG. 8, the exemplary apparatus for producing an EPS includes a reactor 2, an uncondensable gas feeding device 3 configured to feed an uncondensable gas to the reactor 2, a discharge device 4 coupled to the reactor 2, a condenser 5 coupled to the discharge device 4, a separation membrane 1 into which an uncondensed stream from the condenser 5 flows, and a gas-liquid separator 30 coupled to the separation membrane 1. According to one exemplary embodiment, the separation membrane 1 may include a first separation membrane 11 and a second separation membrane 21, as described above. For example, the separation membrane 1 may include the first separation membrane 11, into which an uncondensed stream from the condenser 5 flows, and in which the uncondensed stream is divided into a first permeate stream $F_3$ which passes through the first separation membrane and a first non-permeate stream $F_2$ which does not pass through the first separation membrane and is discharged, and the second separation membrane 21, into which the first non-permeate stream $F_2$ flows, and in which the first non-permeate stream is divided into a second permeate stream $F_5$ which passes through the second separation membrane and a second non-permeate stream $F_4$ which does not pass through the second separation membrane and is discharged. As described above, the first separation membrane 11 and the second separation membrane 21 may have different selectivity and permeability. Also, the first separation membrane 11 and the second separation membrane 21 may satisfy Formulas 1 to 5 as described above in the first embodiment of the apparatus for producing an EPS, and thus have the same effects as described above.

According to one exemplary embodiment, as shown in FIG. 8, the membrane separation device 1 may include the condenser 2, the gas-liquid separator 30 and the pressure regulator, and thus have the same effects as described above.

The present application is also directed to providing a membrane separation method.

According to one exemplary embodiment, the membrane separation method may include feeding a feed stream including a component A and a component B into a first separation membrane 11 to discharge a first permeate stream $F_3$ which passes through the first separation membrane 11 and a first non-permeate stream $F_2$ which does not pass through the first separation membrane 11, and feeding the first non-permeate stream $F_2$ into a second separation membrane 21 to discharge a second permeate stream $F_5$ which passes through the second separation membrane 21 and a second non-permeate stream $F_4$ which does not pass through the second separation membrane 21, The first separation membrane 11 and the second separation membrane 21 may satisfy Formulas 1 to 5 as described above in the membrane separation device, and thus have the same effects as described above.

According to one exemplary embodiment, the membrane separation method may further include condensing the feed stream $F_1$ comprising the component A and the component B before the feed stream is fed into the first separation membrane 11. For example, the feed stream $F_1$ may flow and be condensed in a condenser 3 before the feed stream $F_1$ is fed into the first separation membrane 11, and a condensed stream $F_7$ may be separated from the feed stream $F_1$. Also, an uncondensed stream in the feed stream $F_1$ may be fed into the first separation membrane 11. When the feed stream $F_1$ is condensed before the feed stream $F_1$ flows into the first separation membrane 11, a condensable component in the components to be separated may be separated in advance. Only a mixed gas in a mixture of the component in an uncondensed gas state and the uncondensable gas may flow into the first separation membrane 11, thereby reducing an area of membranes used.

According to one exemplary embodiment, in the membrane separation method of the present application, the first permeate stream $F_3$ and the second permeate stream $F_5$ may also flow into the gas-liquid separator 30 to be divided into a liquid stream and a gas stream. For this purpose, the membrane separation method may further include feeding the separated gas stream $F_6$ into the first separation membrane 11 and/or the second separation membrane 21. As the first permeate stream $F_3$ and the second permeate stream $F_5$ in the membrane separation device 1 flows into the gas-liquid separator 30, the components included in the first permeate stream $F_3$ and the second permeate stream $F_5$ may be gas-liquid separated in the gas-liquid separator 30. Also, the separated gas stream $F_6$ may again flow into the first separation membrane 11 or the second separation membrane 21 to be divided again. In this case, the separated gas stream $F_6$ may be re-used in the membrane separation process to reduce the costs used in this process.

According to one exemplary embodiment, the feeding of the separated gas stream $F_6$ into the first separation membrane 11 and/or the second separation membrane 21 may be performed by applying the same pressure as the pressure of the feed stream to the separated gas stream $F_6$ to feed the separated gas stream $F_6$ into the first separation membrane 11 and/or the second separation membrane 21. The feed stream $F_1$ flowing into the first separation membrane 11 and the first non-permeate stream $F_2$ flowing into the second separation membrane 21 may be high-pressure streams having a higher pressure condition than the gas stream $F_6$ having a normal pressure, and thus the pressure of the gas stream $F_6$ having a normal pressure may be adjusted to the same pressure as the feed stream $F_1$ and/or the first non-permeate stream $F_2$ by means of the pressure device, for example, a compressor, before the gas stream $F_6$ is mixed with the feed stream $F_1$ fed through the first separation membrane 11 and the first non-permeate stream $F_2$ flowing into the second separation membrane 21.

According to one exemplary embodiment, the feeding of the separated gas stream $F_6$ into the first separation membrane 11 and/or the second separation membrane 21 may also be performed by decompressing the first non-permeate stream $F_2$ to the same pressure as in the separated gas stream $F_6$ and feeding the decompressed first non-permeate stream $F_2$ and the separated gas stream $F_6$ into the second separation membrane 21. Since the above-described pressure device should be separately installed to allow the gas stream $F_6$ having the normal pressure to flow into the first separation membrane 11, additional costs may occur. As described above, however, the separated gas stream $F_6$ may be re-used in the membrane separation process without installing an additional pressure device by adjusting a pressure of the first non-permeate stream $F_2$ to a normal pressure by means of the decompression device, thereby maximizing an amount of the components recovered in this process.

The membrane separation method according to one exemplary embodiment of the present application may be used in various fields, and may, for example, be used in an EPS producing process. For example, Since the EPS producing process includes the above-described membrane separation method, pentane used as a foaming agent upon EPS production may be separated and recovered with low costs, thereby realizing an environmentally friendly EPS producing process. Also, the separated VOC may be recycled and re-used in the EPS producing process, thereby reducing the production cost.

The present application is also directed to providing a method for producing an EPS.

According to one exemplary embodiment, the method for producing an EPS includes feeding an uncondensable gas to a reactor in which a polystyrene bead is polymerized and which is filled with an expandable gas, and feeding a mixed stream of an unimpregnated expandable gas and the uncondensable gas to the polystyrene bead into a separation membrane so that the mixed stream is divided into a permeate stream which passes through the separation membrane and a non-permeate stream which does not pass through the separation membrane to discharge the permeate stream and the non-permeate stream.

In the foregoing, the polymerization of the polystyrene bead may be performed in the same manner as described in the above-described apparatus for producing an EPS.

According to one exemplary embodiment, the method for producing an EPS may include feeding the mixed stream of the unimpregnated expandable gas and the uncondensable gas to the polystyrene bead into the first separation membrane 11 to discharge a first permeate stream $F_3$ which passes through the first separation membrane 11 and a first non-permeate stream $F_2$ which does not pass through the first separation membrane 11, and feeding the first non-permeate stream $F_2$ into the second separation membrane 21 to discharge a second permeate stream $F_5$ which passes through the second separation membrane 21 and a second non-permeate stream $F_4$ which does not pass through the second separation membrane.

The first separation membrane 11 and the second separation membrane 21 may satisfy Formulas 1 to 5 as described above in the apparatus for producing an EPS, and thus have the same effects as described above.

According to one exemplary embodiment, the method for producing an EPS may further include condensing the mixed stream of the unimpregnated expandable gas and the uncondensable gas before the mixed stream is fed to the polystyrene bead through the first separation membrane 11. For example, the mixed gas stream including the expandable gas may flow and be condensed in the condenser 3 before the mixed gas stream is fed into the first separation membrane 11, and a condensed stream $F_7$ may be separated from the gas stream including the expandable gas. Also, an uncondensed stream in the gas stream $F_1$ including the expandable gas may be fed into the first separation membrane 11. When the gas stream including the expandable gas, for example, a VOC, is condensed before the gas stream flows into the first separation membrane 11, condensable expandable gas components may be condensed and separated in advance. Only a mixed gas in a mixture of the uncondensed expandable gas component and the uncondensable gas may flow into the first separation membrane 11, thereby reducing an area of membranes used.

According to one exemplary embodiment, in the method for producing an EPS according to the present application, the first permeate stream $F_3$ and the second permeate stream $F_5$ may also flow into the gas-liquid separator 30 so that the first permeate stream $F_3$ and the second permeate stream $F_5$ are divided into a liquid stream and a gas stream. For this purpose, the method for producing an EPS may further include feeding the separated gas stream $F_6$ into the first separation membrane 11 and/or the second separation membrane 21. As the first permeate stream $F_3$ and the second permeate stream $F_5$ in the membrane separation device 1 flows into the gas-liquid separator 30, the components included in the first permeate stream $F_3$ and the second permeate stream $F_5$ may be gas-liquid separated in the gas-liquid separator 30. Also, the separated gas stream may again flow into the first separation membrane 11 or the second separation membrane 21 to be divided again. In this case, the separated gas stream $F_6$ may be re-used in the membrane separation process to reduce the costs used in this process.

According to one exemplary embodiment, the feeding of the separated gas stream $F_6$ into the first separation membrane 11 and/or the second separation membrane 21 may be performed by applying the same pressure as the pressure of the feed stream to the separated gas stream $F_6$ to feed the separated gas stream $F_6$ into the first separation membrane 11 and/or the second separation membrane 21. The feed stream $F_1$ flowing into the first separation membrane 11 and the first non-permeate stream $F_2$ flowing into the second separation membrane 21 may be high-pressure streams having a higher pressure condition than the gas stream $F_6$ having a normal pressure, and thus the pressure of the gas stream $F_6$ having a normal pressure may be adjusted to the same pressure as the feed stream $F_1$ and/or the first non-permeate stream $F_2$ by means of the pressure device, for example, a compressor, before the gas stream $F_6$ is mixed with the feed stream $F_1$ fed into the first separation membrane 11 and the first non-permeate stream $F_2$ flowing into the second separation membrane 21.

According to one exemplary embodiment, the feeding of the separated gas stream $F_6$ into the first separation membrane 11 and/or the second separation membrane 21 may also be performed by decompressing the first non-permeate stream $F_2$ to the same pressure as in the separated gas stream $F_6$ and feeding the decompressed first non-permeate stream $F_2$ and the separated gas stream $F_6$ into the second separation membrane 21. Since the above-described pressure device should be separately installed to allow the gas stream $F_6$ having the normal pressure to flow into the first separation membrane 11, additional costs may occur. As described above, however, the separated gas stream $F_6$ may be re-used in the membrane separation process without installing an additional pressure device by adjusting a pressure of the first non-permeate stream $F_2$ to a normal pressure by means of the decompression device, thereby maximizing an amount of the components recovered in this process.

According to method for producing an EPS according to one exemplary embodiment of the present application, pentane used as a foaming agent upon EPS production may be separated and recovered with low costs, thereby realizing an environmentally friendly EPS producing process. Also, the separated VOC may be recycled and re-used in the EPS producing process, thereby reducing the production cost.

Advantageous Effects

According to the membrane separation device and method according to the exemplary embodiments of the present application, the separation membranes having a small area can be used to separate a component to be separated with high selectivity, thereby remarkably improving processing efficiency and economic efficiency. According to the apparatus and method for producing an EPS according to the exemplary embodiments of the present application, the separation membranes having a small area can also be used to separate an expandable gas component to be separated, especially a volatile organic compound (VOC), with high selectivity, thereby remarkably improving processing efficiency and economic efficiency. Also, the VOC can be separated and recovered, thereby preventing environmental pollution caused by global warming.

DESCRIPTION OF DRAWINGS

FIG. 1 is a schematic diagram showing a first embodiment of a membrane separation device according to the present application.

FIGS. 2 to 4 are schematic diagrams showing various embodiments of the membrane separation device according to one exemplary embodiment of the present application.

FIG. 5 is a schematic diagram showing an apparatus for producing an expandable polystyrene according to one exemplary embodiment of the present application.

FIGS. 6 to 8 are schematic diagrams showing various embodiments of the apparatus for producing an expandable polystyrene according to one exemplary embodiment of the present application.

FIG. 9 is a schematic diagram showing a membrane separation device including only a first separation membrane according to one exemplary embodiment of the present application.

FIG. 10 is a schematic diagram showing a membrane separation device including only a second separation membrane according to one exemplary embodiment of the present application.

FIG. 11 is a graph illustrating the content of pentane in a mixed gas of unimpregnated pentane and nitrogen, which is introduced into the apparatus for producing an EPS according to Example 6 of the present application, with the lapse of time.

FIG. 12 is a graph illustrating the content of pentane in a mixed gas of unimpregnated pentane and nitrogen, which is introduced into the apparatus for producing an EPS according to Example 7 of the present application, with the lapse of time.

BEST MODE

Hereinafter, the present application will be described in further detail with reference to Examples according to the present application and Comparative Examples not according to the present application. However, it should be understood that the Examples and Comparative Examples described below are not intended to limit the scope of the present application.

Separation of Pentane Using Membrane Separation Device Including Only One Separation Membrane Example 1

A membrane separation process was performed by allowing a mixed gas (pentane content: 12.7 mol %) of pentane and nitrogen to flow into the membrane separation device as shown in FIG. 9, which included only a first separation membrane having high selectivity to the pentane gas, at a gauge pressure of 4.0 kgf/cm² and a flow rate pf 4.1 kg/hr. The permeabilities of pentane (component A) and nitrogen (component B) in the first separation membrane were $P^1_A$=56.2 GPU and $P^1_B$=0.5 GPU, respectively, as calculated by Equation 1. Also, the selectivity of pentane (component A) to nitrogen (component B) in the first separation membrane was $\alpha^1_{AB}$=115, as calculated by Equation 2. In this case, the content of pentane in the first non-permeate stream discharged without passing through the first separation membrane was measured to be 3.9 mol %, and the recovery rate of pentane (component A) in the membrane separation device was calculated to be 72%, as calculated by the following Equation 3.

Recovery rate (%)=flow rate (kg/hr) of recovered component $A$/flow rate (kg/hr) of introduced component $A$×100     [Equation 3]

Example 2

A membrane separation process was performed in the same manner as in Example 1, except that a mixed gas (pentane content: 12.9 mol %) of pentane and nitrogen was allowed to flow into the membrane separation device as shown in FIG. 10, which included only a second separation membrane having high permeability to the pentane gas, at a gauge pressure of 4.0 kgf/cm² and a flow rate of 3.8 kg/hr. The permeabilities of pentane (component A) and nitrogen (component B) in the second separation membrane were $P^2_A$=244.5 GPU and $P^2_B$=3.3 GPU, respectively, as calculated by Equation 1. Also, the selectivity of pentane (component A) to nitrogen (component B) in the second separation membrane was $\alpha^2_{AB}$=73.4, as calculated by Equation 2. In this case, the content of pentane in the second non-permeate stream discharged without passing through the second separation membrane was measured to be 0.4 mol %, and the recovery rate of pentane (component A) in the membrane separation device was calculated to be 97%, as calculated by the following Equation 3.

Separation of Pentane Using Membrane Separation Device Including Two Separation Membranes Having Different Selectivity and Permeability Example 3

A membrane separation process was performed in the same manner as in Example 1, except that a mixed gas (pentane content: 13.4 mol %) of pentane and nitrogen was allowed to flow into a membrane separation device in which the first separation membrane used in Example 1 and the second separation membrane used in Example 2 were coupled as shown in FIG. 1 at a gauge pressure of 4.0 kgf/cm² and a flow rate of 4.1 kg/hr. The content of pentane in the second non-permeate stream discharged without passing through the second separation membrane was measured to be 0.2 mol %, and the recovery rate of pentane (component A) in the membrane separation device was calculated to be 99%, as calculated by the following Equation 3.

Example 4

A membrane separation process was performed in the same manner as in Example 3, except that a mixed gas (pentane content: 20.0 mol %, and gas temperature: 51° C.) of pentane and nitrogen was allowed to flow into a condenser at a gauge pressure of 4.0 kgf/cm² and a flow rate of 11.2 kg/hr, as shown in FIG. 2, and condensed. A condensed stream $F_7$ emitted from the condenser was separately separated, and an uncondensed expandable gas stream (pentane content: 13.1 mol %, and gas temperature: 15° C.) was allowed to flow into the membrane separation device in which the first separation membrane and the second separation membrane were coupled as shown in FIG. 2 at a flow rate of 6.4 kg/hr.

The recovery rate of pentane (component A) recovered from the condenser was measured to be 59%. Also, the content of pentane in the second non-permeate stream discharged without passing through the second separation membrane was measured to be 0.7 mol %, and the recovery rate of pentane (component A) in the membrane separation device was calculated to be 95%, as calculated by Equation 3. As a result, the total recovery rate of pentane using the condenser and the membrane separation device was measured to be 98%.

Example 5

A membrane separation process was performed in the same manner as in Example 3, except that a mixed gas (pentane content: 28.4 mol %, and gas temperature: 53° C.) of pentane and nitrogen was allowed to flow into a condenser at a gauge pressure of 4.5 kgf/cm² and a flow rate of 9.7 kg/hr, as shown in FIG. 4, and condensed. A condensed stream $F_7$ emitted from the condenser was separately separated, and an uncondensed expandable gas stream (pentane content: 12.2 mol %, and gas temperature: 15° C.) was allowed to flow into the membrane separation device in which the first separation membrane, the second separation membrane and the gas-liquid separator were coupled as shown in FIG. 4 at a flow rate of 6.5 kg/hr.

The recovery rate of pentane (component A) recovered from the condenser was calculated to be 66%. Also, the content of pentane in the second non-permeate stream discharged without passing through the second separation membrane was measured to be 0.036 mol %, and the recovery rate of pentane (component A) in the membrane separation device was calculated to be 99.8%, as calculated by Equation 3. As a result, the total recovery rate of pentane using the condenser and the membrane separation device was measured to be 99.9%.

Simulation Test for Pentane Separation Process Using Membrane Separation Device Including Two Separation Membranes Having Different Selectivity and Permeability Experimental Example 1

A simulation test for the membrane separation process was performed by allowing a mixed gas (pentane content: 15.2 mol %) of pentane and nitrogen to flow into the membrane separation device in which the first and second separation membranes satisfying the following requirements were coupled at a gauge pressure of 3.0 kgf/cm² and a flow rate of 1.4 Nm³/hr. In this case, the recovery rate of pentane (component A) in the membrane separation device was calculated to be 96%, as calculated by Equation 3.

<Requirements for Separation Membranes>

First separation membrane: the permeabilities of pentane (component A) and nitrogen (component B) are $P^1_A=50$ GPU and $P^1_B=0.17$ GPU, respectively, as calculated by Equation 1, and the selectivity of pentane (component A) to nitrogen (component B) in the first separation membrane is $\alpha^1_{AB}=300$, as calculated by Equation 2.

Second separation membrane: the permeabilities of pentane (component A) and nitrogen (component B) are $P^2_A=300$ GPU and $P^2_B=6$ GPU, respectively, as calculated by Equation 1, and the selectivity of pentane (component A) to nitrogen (component B) in the second separation membrane is $\alpha^2_{AB}=50$, as calculated by Equation 2.

Comparative Experimental Example 1

A simulation test for the membrane separation process was performed in the same manner as in Experimental Example 1, except that a mixed gas (pentane content: 15.2 mol %) of pentane and nitrogen was allowed to flow into the membrane separation device, in which the first separation membrane and the second separation membrane were coupled so that the mixed gas flowed into the second separation membrane used in Experimental Example 1 and a non-permeate stream which did not pass through the second separation membrane flowed into the first separation membrane used in Experimental Example 1. In this case, the recovery rate of pentane (component A) in the membrane separation device was calculated to be 94%, as calculated by Equation 3.

Separation of Pentane Gas in EPS Producing Process Using Separation Membranes

Example 6

A dispersion prepared by mixing 269 kg of a styrene monomer, 4 kg of a polystyrene recycle bead (molecular weight: 200,000 to 300,000), 1.16 kg of benzoyl peroxide, 0.13 kg of t-butyl perbenzoate, 0.8 kg of dicumylperoxide as an initiator, 0.06 kg of divinylbenzene as a molecular weight modifier, and 1.27 kg of hexabromocyclododecane as a flame retardant, was put into a 700-L high-pressure reactor, and stirred. Thereafter, 0.28 kg of tricalcium phosphate was added as a dispersing agent together with 219 L of ionic water, and stirred.

The reactor was hermetically sealed, and the inside of the reactor was heated to a temperature of 90° C. for 90 minutes. After heating for an hour, 0.03 kg of an aqueous potassium persulfate having 1% TSC was added as a dispersing aid. When the inner temperature of the reactor reached 90° C., the inside of the reactor was maintained at 90° C. for 210 minutes. Meanwhile, 0.3 kg of tricalcium phosphate as a pH control agent, and 0.007 kg of polyoxyethylene sorbitan monolaurate as a surfactant, were put into the reactor. After the inner temperature of the reactor was maintained at 90° C. for 260 minutes, 25 kg of pentane as a foaming agent, was added, the inside of the reactor was heated to a temperature of 100° C. for 50 minutes, and the inner temperature of the reactor was maintained for 40 minutes. Then, the inside of the reactor was heated to a temperature of 125° C. for 50 minutes, the inner temperature of the reactor was maintained for 150 minutes, and the reactor was then cooled. The inner pressure of the reactor decreased as the reactor was cooled. When the inner gauge pressure of the reactor reached 3.1 kgf/cm², nitrogen having a gauge pressure of 4.8 kgf/cm² was fed to the reactor. Subsequently, when the inner gauge pressure of the reactor was kept constant at 3.5 kgf/cm², the mixed gas of unimpregnated pentane and nitrogen was discharged from the reactor by means of the discharge device, and put into a condenser whose gauge pressure was set at 3.5 kgf/cm² and which was cooled to 15° C. at a flow rate of 6.0 kg/hr, and a portion of pentane was condensed. A condensed stream $F_7$ emitted from the condenser was separately separated, and the mixed stream of uncondensed pentane gas and nitrogen gas was allowed to flow into the membrane separation device including only the first separation membrane used in Example 1 at a flow rate of 5.4 kg/hr.

The content of pentane in the first non-permeate stream discharged without passing through the first separation membrane was measured to be less than 4 mol %. FIG. 11 is a graph illustrating the content of pentane in a mixed gas of unimpregnated pentane and nitrogen with the lapse of time.

Example 7

An expandable polystyrene was produced in the same manner as in Example 6, except that nitrogen having a gauge pressure of 4.8 kgf/cm² was fed to the reactor when the inner gauge pressure of the reactor reached 3.8 kgf/cm² as the reactor was cooled, a mixed gas of unimpregnated pentane and nitrogen was emitted from the reactor by means of the discharge device when the inner gauge pressure of the reactor was kept constant at 4.0 kgf/cm², and the mixed gas was put into a condenser whose gauge pressure was set at 4.0 kgf/cm² and which was cooled to 15° C. at a flow rate of 6.6 kg/hr and a portion of pentane was condensed, as shown in FIG. 8. A condensed stream $F_7$ emitted from the condenser was separately separated, and the mixed stream of uncondensed pentane gas and nitrogen gas was allowed to flow into the membrane separation device, in which the first separation membrane, the second separation membrane and the gas-liquid separator used in Example 1 were coupled as shown in FIG. 8, at a flow rate of 5.6 kg/hr. In this case, the mixed stream was allowed to flow into the second separation membrane with controlling the non-permeate stream of the first separation membrane to a normal pressure, and the separated gas stream in the gas-liquid separator was circulated to the second separation membrane.

The content of pentane in the second non-permeate stream discharged without passing through the second separation membrane was measured to be less than 1 mol %. FIG. 12 is a graph illustrating the content of pentane in a mixed gas of unimpregnated pentane and nitrogen, which is introduced into the apparatus for producing an EPS shown in FIG. 8, with the lapse of time.

The invention claimed is:

1. A membrane separation device comprising:
    a first separation membrane, into which a feed stream flows, and in which the feed stream is divided into a first permeate stream which passes through the first separation membrane and a first non-permeate stream which does not pass through the first separation membrane and the first permeate stream and the first non-permeate stream are discharged;
    a second separation membrane, into which the first non-permeate stream flows, and in which the first non-permeate stream is divided into a second permeate stream which passes through the second separation membrane and a second non-permeate stream which does not pass through the second separation membrane and the second permeate stream and the second non-permeate stream are discharged;
    a gas-liquid separator coupled to a front end of the first separation membrane and/or coupled between the first separation membrane and the second separation membrane to divide the first permeate stream and the second permeate stream into a gas stream and a liquid stream, discharge the divided gas stream and allow the gas stream to flow into the first separation membrane and/or second separation membrane together with the feed stream or the first non-permeate stream, and
    a decompression device that decompresses the first non-permeate stream,
    wherein the gas-liquid separator is coupled so that the gas stream discharged from the gas-liquid separator flows into the second separation membrane together with the first non-permeate stream, and
    wherein the first separation membrane and the second separation membrane have different selectivities and permeabilities with each other with respect to the at least two components.

2. The membrane separation device of claim 1, wherein the first separation membrane and the second separation membrane satisfy the following Formulas 1 and 2:

$$\alpha^1_{AB} - \alpha^2_{AB} > 0 \qquad \text{[Formula 1]}$$

$$P^2_A - P^1_A > 0 \qquad \text{[Formula 2]}$$

wherein $\alpha^1_{AB}$ represents a selectivity ($P^1_A/P^1_B$) of a component A to a component B present in the feed stream flowing into the first separation membrane,
$\alpha^2_{AB}$ represents a selectivity ($P^2_A/P^2_B$) of the component A to the component B present in the first non-permeate stream flowing into the second separation membrane,
$P^1_A$ and $P^1_B$ represent permeabilities of the component A and the component B present in the feed stream flowing into the first separation membrane, respectively, and
$P^2_A$ and $P^2_B$ represent permeabilities of the component A and the component B present in the first non-permeate stream flowing into the second separation membrane, respectively, wherein the component A represents a component to be separated from among components flowing into each separation membrane, and the component B represents the other component with the exception of the component A from among the components flowing into each separation membrane.

3. The membrane separation device of claim 2, wherein the first separation membrane and the second separation membrane satisfy the following Formulas 3 and 4:

$$\alpha^1_{AB} > 1 \qquad \text{[Formula 3]}$$

$$\alpha^2_{AB} > 1 \qquad \text{[Formula 4]}$$

wherein $\alpha^1_{AB}$ and $\alpha^2_{AB}$ are as defined in claim 2.

4. The membrane separation device of claim 1, further comprising a pressure device configured to apply a pressure to the gas stream before the gas stream discharged from the gas-liquid separator flows into the first separation membrane and/or the second separation membrane.

5. An apparatus for producing an expandable polystyrene, comprising:
    a reactor, and
    the membrane separation device defined in claim 1,
    wherein the reactor is filled with an expandable gas and a portion of the expandable gas is impregnated in polystyrene beads in the reactor,
    wherein the membrane separation device separates an unimpregnated expandable gas discharged from the reactor.

6. A membrane separation device comprising:
    a condenser in which a feed stream including at least two components flows;
    a first separation membrane, into which an uncondensed stream from the condenser flows, and in which the uncondensed stream is divided into a first permeate stream which passes through the first separation membrane and a first non-permeate stream which does not pass through the first separation membrane and the first permeate stream and the first non-permeate stream are discharged;
    a second separation membrane into which the first non-permeate stream flows, and in which the first non-permeate stream is divided into a second permeate stream which passes through the second separation membrane and a second non-permeate stream which does not pass through the second separation membrane and the second permeate stream and the second non-permeate stream are discharged; and
    a gas-liquid separator coupled to a front end of the first separation membrane and/or coupled between the first separation membrane and the second separation membrane to divide the first permeate stream and the second permeate stream into a gas stream and a liquid stream, discharge the divided gas stream and allow the gas stream to flow into the first separation membrane and/or second separation membrane together with the feed stream or the first non-permeate stream; and
    a decompression device that decompresses the first non-permeate stream,
    wherein the gas-liquid separator is coupled so that the gas stream discharged from the gas-liquid separator flows into the second separation membrane together with the first non-permeate stream, and
    wherein the first separation membrane and the second separation membrane have different selectivities and permeabilities with each other with respect to the at least two components.

7. The membrane separation device of claim 6, wherein the first separation membrane and the second separation membrane satisfy the following Formulas 1 and 2:

$$\alpha^1_{AB} - \alpha^2_{AB} > 0 \qquad \text{[Formula 1]}$$

$$P^2_A - P^1_A > 0 \qquad \text{[Formula 2]}$$

wherein $\alpha^1_{AB}$ represents a selectivity ($P^1_A/P^1_B$) of a component A to a component B present in the uncondensed stream flowing into the first separation membrane, $\alpha^2_{AB}$ represents a selectivity ($P^2_A/P^2_B$) of the component A to the component B present in the first non-permeate stream flowing into the second separation membrane, $P^1_A$ and $P^1_B$ represent permeabilities of the component A and the component B present in the uncondensed stream flowing into the first separation membrane, respectively, and $P^2_A$ and $P^2_B$ represent permeabilities of the component A and the component B present in the first non-permeate stream flowing into the second separation membrane, respectively, wherein the component A represents a component to be separated from among components flowing into each separation membrane, and the component B represents the other component with the exception of the component A from among the components flowing into each separation membrane.

8. The membrane separation device of claim 7, wherein the first separation membrane and the second separation membrane satisfy the following Formulas 3 and 4:

$$\alpha^1_{AB} > 1 \qquad \text{[Formula 3]}$$

$$\alpha^2_{AB} > 1 \qquad \text{[Formula 4]}$$

wherein $\alpha^1_{AB}$ and $\alpha^2_{AB}$ are as defined in claim 7.

9. The membrane separation device of claim 6, further comprising a pressure device configured to apply a pressure to the gas stream before the gas stream discharged from the gas-liquid separator flows into the first separation membrane and/or the second separation membrane.

* * * * *